US010232138B2

(12) United States Patent
Acker et al.

(10) Patent No.: US 10,232,138 B2
(45) Date of Patent: *Mar. 19, 2019

(54) SYSTEMS AND METHOD FOR DELIVERY OF THERAPEUTIC GAS TO PATIENTS IN NEED THEREOF USING ENHANCED BREATHING CIRCUIT GAS (BCG) FLOW MEASUREMENT

(71) Applicant: Mallinckrodt Hospital Products IP Limited, Dublin (IE)

(72) Inventors: Jaron M. Acker, Madison, WI (US); Craig R. Tolmie, Stoughton, WI (US)

(73) Assignee: Mallinckrodt Hospital Product IP Limited, Dublin (IE)

( * ) Notice: Subject to any disclaimer, the term of this patent is extended or adjusted under 35 U.S.C. 154(b) by 616 days.

This patent is subject to a terminal disclaimer.

(21) Appl. No.: 14/674,327

(22) Filed: Mar. 31, 2015

(65) Prior Publication Data
US 2015/0273176 A1    Oct. 1, 2015

Related U.S. Application Data

(63) Continuation of application No. 14/672,447, filed on Mar. 30, 2015.
(Continued)

(51) Int. Cl.
*A61M 16/12* (2006.01)
*A61M 16/20* (2006.01)
(Continued)

(52) U.S. Cl.
CPC ...... *A61M 16/122* (2014.02); *A61M 16/0003* (2014.02); *A61M 16/0051* (2013.01);
(Continued)

(58) Field of Classification Search
CPC ............. A61M 16/00; A61M 16/0003; A61M 16/0051; A61M 16/0057; A61M 16/009;
(Continued)

(56) References Cited

U.S. PATENT DOCUMENTS

| 5,558,083 A | 9/1996 | Bathe et al. |
| 5,732,693 A | 3/1998 | Bathe et al. |

(Continued)

FOREIGN PATENT DOCUMENTS

| EP | 0872254 | 10/1998 |

OTHER PUBLICATIONS

PCT International Search Report and Written Opinion in PCT/US2015/023794, dated Jun. 8, 2015, 8 pages.
(Continued)

*Primary Examiner* — Annette Dixon

(57) ABSTRACT

The present invention generally relates to systems and method for delivery of therapeutic gas to patients in need thereof using enhanced breathing circuit gas (BCG) flow measurement. At least some of these enhanced BCG flow measurements can be used to address some surprising phenomena that may, at times, occur when wild stream blending therapeutic gas into breathing gas that a patient receives from a breathing circuit affiliated with a ventilator. Utilizing at least some of these enhanced BCG flow measurements the dose of therapeutic gas wild stream blended into breathing gas that the patient receives from a ventilator can at least be more accurate and/or over delivery of therapeutic gas into the breathing gas can be avoided and/or reduced.

20 Claims, 8 Drawing Sheets

Related U.S. Application Data

(60) Provisional application No. 61/973,544, filed on Apr. 1, 2014.

(51) Int. Cl.
  *A61M 16/00* (2006.01)
  *A61M 16/08* (2006.01)
  *A61M 16/06* (2006.01)
  *A61M 16/10* (2006.01)
  *A61M 16/01* (2006.01)

(52) U.S. Cl.
  CPC .......... *A61M 16/01* (2013.01); *A61M 16/024* (2017.08); *A61M 16/06* (2013.01); *A61M 16/0883* (2014.02); *A61M 16/0891* (2014.02); *A61M 16/1005* (2014.02); *A61M 16/12* (2013.01); *A61M 16/20* (2013.01); *A61M 16/0666* (2013.01); *A61M 16/085* (2014.02); *A61M 2016/003* (2013.01); *A61M 2016/0039* (2013.01); *A61M 2016/102* (2013.01); *A61M 2016/103* (2013.01); *A61M 2202/0241* (2013.01); *A61M 2202/0275* (2013.01); *A61M 2205/18* (2013.01); *A61M 2205/3334* (2013.01); *A61M 2205/3368* (2013.01); *A61M 2205/502* (2013.01); *A61M 2205/52* (2013.01)

(58) Field of Classification Search
  CPC .. A61M 16/01; A61M 16/04; A61M 16/0666; A61M 16/0808; A61M 16/0816; A61M 16/0833; A61M 16/085; A61M 16/0875; A61M 16/10; A61M 16/1005; A61M 16/1015; A61M 16/104; A61M 16/107; A61M 16/12; A61M 16/122; A61M 16/125; A61M 16/16; A61M 16/20; A61M 16/201; A61M 16/202; A61M 16/203; A61M 16/204; A61M 16/205; A61M 16/208; A61M 16/22; A61M 2016/0021; A61M 2016/0024; A61M 2016/0027; A61M 2016/003; A61M 2016/0033; A61M 2016/0039; A61M 2016/0042; A61M 2016/102; A61M 2016/1025; A61M 2016/1035; A61M 2202/0007; A61M 2202/0208; A61M 2202/0233; A61M 2202/025; A61M 2202/0266; A61M 2202/0275; A61M 2202/0283; A61M 2205/18; A61M 2205/27; A61M 2205/33; A61M 2205/3327; A61M 2205/3334; A61M 2205/3375; A61M 2205/35; A61M 2205/3561; A61M 2205/3569; A61M 2205/3592; A61M 2205/3606; A61M 2205/50; A61M 2205/502; A61M 2205/505; A61M 2205/52; A61M 2205/581; A61M 2205/583; A61M 2205/584; A61M 2205/60; A61M 2205/6009; A61M 2205/6072; A61M 2205/8206; A61M 2205/8212; A61M 2205/8237; A61M 2209/082; A61M 2209/084; A61M 2210/0681; A61M 2230/005; A61M 2230/42; A61M 2230/435; A61B 5/02007; A61B 5/0205; A61B 5/08; A61B 5/087; A61B 5/4839; A61B 5/6819; A61B 5/7275; A61B 5/7278

USPC .......... 128/200.24, 202.22, 202.26, 203.12, 128/203.14, 203.22, 203.24, 203.25, 128/203.29, 204.18, 204.21, 204.22, 128/204.23, 205.24
  See application file for complete search history.

(56) References Cited

U.S. PATENT DOCUMENTS

| | | | |
|---|---|---|---|
| 5,752,504 A | 5/1998 | Bathe | |
| 6,125,846 A | 10/2000 | Bathe et al. | |
| 6,186,142 B1* | 2/2001 | Schmidt | A61M 16/08 128/204.23 |
| 6,581,599 B1* | 6/2003 | Stenzler | A61M 16/12 128/203.12 |
| 7,523,752 B2 | 4/2009 | Montgomery et al. | |
| 7,955,294 B2* | 6/2011 | Stenzler | A61K 33/00 128/203.12 |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,381,729 B2* | 2/2013 | Freitag | A61M 16/16 128/207.14 |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2005/0172966 A1* | 8/2005 | Blaise | A61M 16/12 128/204.21 |
| 2006/0207594 A1* | 9/2006 | Stenzler | A61M 16/12 128/204.18 |
| 2007/0181126 A1 | 8/2007 | Tolmie et al. | |
| 2010/0252037 A1* | 10/2010 | Wondka | A61M 16/0666 128/203.12 |
| 2012/0180789 A1 | 7/2012 | Tobia et al. | |
| 2013/0118486 A1* | 5/2013 | Schnitman | A61M 16/0051 128/202.22 |
| 2015/0273175 A1* | 10/2015 | Acker | A61M 16/01 128/203.14 |
| 2015/0314101 A1* | 11/2015 | Acker | A61M 16/201 128/203.14 |
| 2015/0320952 A1* | 11/2015 | Acker | A61M 16/0051 128/202.22 |

OTHER PUBLICATIONS

PCT Annex to Form PCT/ISA/206 Communication Relating to the Results of the Partial Search Report in PCT/US2015/023794, dated Jun. 8, 2015, 8 pages.
Flow Measurement with Respironics Flow Sensors, Apr. 30, 2011, 7 pages.
INOmax DS (Delivery System): Operation Manual (800 ppm INOMAX (nitric oxide) for Inhalation), Ikaria, Inc. 2010, 112 pages.
INOvent Delivery System: Operation and Maintenance Manual (CGA Variant), Datex-Ohmeda, Inc. 2000, 180 pages.
Using the INOpulse DS Subject Guide, Ikaria, Inc. 2012, 50 pages.
INOmax Label, Nitric Oxide Gas, INO Therapeutics 2013, 2 pages.
INOmax DSIR (Delivery System): Operation Manual (800 ppm INOMAX (nitric oxide) for Inhalation), Ikaria, Inc. 2012, 136 pages.

* cited by examiner

SYSTEMS AND METHOD FOR DELIVERY OF THERAPEUTIC GAS TO PATIENTS IN NEED THEREOF USING ENHANCED BREATHING CIRCUIT GAS (BCG) FLOW MEASUREMENT

CROSS-REFERENCE TO RELATED APPLICATIONS

This application is a continuation under 35 U.S.C. § 120 of U.S. patent application Ser. No. 14/672,447, filed Mar. 30, 2015, which claims the benefit under 35 U.S.C. § 119(e) to U.S. Provisional Application No. 61/973,544, filed Apr. 1, 2014, the entire contents of which are incorporated herein by reference in their entirety.

FIELD

The present invention generally relates to systems and method for delivery of therapeutic gas to patients in need thereof using enhanced breathing circuit gas (BCG) flow measurement.

BACKGROUND

Therapeutic gas can be delivered to patients, in need thereof, to provide medical benefits. One such therapeutic gas is nitric oxide (NO) gas that, when inhaled, acts to dilate blood vessels in the lungs, improving oxygenation of the blood and reducing pulmonary hypertension. Because of this, nitric oxide can be provided as a therapeutic gas in the inspiratory breathing gases for patients with pulmonary hypertension.

Many of these patients who may benefit from nitric oxide gas receive breathing gas from a breathing circuit affiliated with a ventilator (e.g., constant flow ventilator, variable flow ventilator, high frequency ventilator, bi-level positive airway pressure ventilator or BiPAP ventilator, etc.). To provide nitric oxide to a patient who receives breathing gas from a ventilator, nitric oxide may be injected into the breathing gas flowing in the breathing circuit. Using this technique the desired dose of the nitric oxide may be based on the concentration of the nitric oxide in the breathing gas, for example, after the nitric oxide has been injected into and/or blending with the breathing gas.

The above, and similar, techniques used to deliver nitric oxide into breathing gas flowing in the breathing circuit can present substantial challenges. For example, providing accurate and/or precise doses of nitric oxide to the patient can be substantially challenging as the breathing gas can have unknown and/or inconsistent flow profiles. This can complicate accurately and/or precisely delivering nitric oxide to the patient at desired doses as it may be substantially difficult to ensure the nitric oxide is delivered at the desired concentration (e.g. set dose). Further, delivering nitric oxide at the desired dose can be substantially important, for example, as dosing can substantially impact safety and efficacy.

Accordingly, a need exists to at least ensure accurate and/or precise dosing of nitric oxide delivered to patient who, for example, may be receiving breathing gas from a breathing circuit affiliated with a ventilator.

SUMMARY

Aspects of the present invention relate to an injector module for delivering nitric oxide (e.g., from a nitric oxide delivery system) into the inspiratory limb of a breathing circuit (affiliated with a ventilator). In one or more embodiments the injector module includes and/or is in communication with a bi-directional breathing circuit gas (BCG) flow sensor capable of measuring forward flowing breathing gas and reverse flowing breathing gas. Using this bi-directional BCG flow sensor and/or information communicated from the bi-directional BCG flow sensor to the nitric oxide delivery system, the nitric oxide delivery system can deliver NO to the injector module more accurately such that under delivery and/or over delivery of therapeutic gas into the breathing gas can be avoided and/or reduced.

In exemplary embodiments, aspects of the present invention can improve breathing circuit flow profile detection capability and/or nitric oxide delivery compensation algorithms can reduce and/or eliminate at least some aspects of breathing circuit gas flow profile controls. This can improve patient safety, lowers probability for user-error (e.g. wrong check valve), and/or provide additional benefits.

The bi-directional BCG flow sensor can be used to address at least a surprising reverse BCG flow phenomena discovered by applicant.

Accordingly, one aspect of the present invention relates to a method of administering therapeutic gas to a patient, the method comprising: measuring flow of a breathing circuit gas through and/or in fluid communication with a breathing circuit affiliated with a ventilator, wherein flow is in a forward direction when flowing from the ventilator towards the patient and in a reverse direction when flowing from the patient towards the ventilator: determining the breathing circuit gas flow is in the forward direction and delivering a therapeutic gas into the breathing circuit gas: determining the breathing circuit gas flow is in the reverse direction and ceasing delivery of the therapeutic gas into the breathing circuit gas; and determining the breathing circuit gas resumed flow in the forward direction and resuming delivery of the therapeutic gas into the breathing circuit gas after compensating for at least a portion of the flow in the reverse direction.

In one or more embodiments, compensating for at least a portion of the flow in the reverse direction comprises not delivering therapeutic gas into the breathing circuit until after an amount of forward flow has been measured equaling the reverse flow measured.

In one or more embodiments, compensating for at least a portion of the flow in the reverse direction comprises comparing the volume of the flow in the reverse direction to a dead space volume and not delivering therapeutic gas into the breathing circuit until after an amount of forward flow has been measured equaling the lesser of (i) the reverse flow measured or (ii) the dead space volume. In some embodiments, the dead space volume is entered by a user and/or is communicated from the ventilator.

In one or more embodiments, the method optionally further comprises providing instructions to a user to add a segment of breathing circuit between the patient and at least one bi-directional BCG flow sensor for measuring the flow of the breathing circuit gas.

In one or more embodiments, the method further comprises receiving information indicative of and/or determining a ventilator type. In one or more embodiments, receiving and/or determining the ventilator type comprises receiving and/or determining whether or not the ventilator is a BiPAP ventilator and/or affiliated with single limb breathing circuit; and compensating for at least a portion of the flow in the reverse direction is based on the receiving and/or determining whether or not the ventilator is a BiPAP ventilator and/or affiliated with single limb breathing circuit.

In one or more embodiments, if the ventilator is a BiPAP ventilator and/or affiliated with single limb breathing circuit, compensating for at least a portion of the flow in the reverse direction comprises not delivering therapeutic gas into the breathing circuit until after an amount of forward flow has been measured equaling at least a portion of the reverse flow measured. In one or more embodiments, not delivering therapeutic gas into the breathing circuit until after an amount of forward flow has been measured equaling at least a portion of the reverse flow measured comprises not delivering therapeutic gas into the breathing circuit until after an amount of forward flow has been measured equaling the lesser of (i) the reverse flow measured or (ii) a dead space volume.

In one or more embodiments, if the ventilator is not a BiPAP ventilator and/or affiliated with a single limb breathing circuit, compensating for at least a portion of the flow in the reverse direction comprises not delivering therapeutic gas into the breathing circuit until after an amount of forward flow has been measured equaling the reverse flow measured.

In some embodiments, the flow measurement is from the ventilator.

In one or more embodiments, the method further comprises measuring carbon dioxide in at least a portion of the reverse flow measured. In some embodiments. compensating for at least a portion of the flow in the reverse direction comprises delivering therapeutic gas into the breathing circuit for the reverse flow measured that contains carbon dioxide and not delivering therapeutic gas into the breathing circuit for the reverse flow measured that does not contain carbon dioxide.

In one or more embodiments, the flow of the breathing circuit gas through and/or in fluid communication with the breathing circuit affiliated with the ventilator is measured by at least one bi-directional BCG flow sensor. and the bi-directional BCG flow sensor one or more of (i) has an operating range for forward flow that is greater than an operating range for reverse flow and (ii) has separate calibration data sets and/or calibration routines for forward and reverse flow.

Another aspect of the present invention relates to a nitric oxide delivery system. In various embodiments, the nitric oxide delivery system comprises an injector module for delivering therapeutic gas into breathing gas in a breathing circuit. The injector module may comprise: an injector body having a first opening and a second opening, the first opening and the second opening being configured to couple the injector module to a patient breathing circuit; a therapeutic gas inlet configured to receive therapeutic gas and enable injection of the therapeutic gas into breathing circuit gas flowing through the injector module; and at least one bi-directional BCG flow sensor capable of measuring breathing circuit gas flow in a forward direction and in a reverse direction. The nitric oxide delivery system may also comprise a control module for providing the therapeutic gas to the therapeutic gas inlet, and the control module being in communication with the at least one bi-directional BCG flow sensor. In one or more embodiments, when the at least one bi-directional BCG flow sensor measures flow in the reverse direction, therapeutic gas is not delivered into the breathing circuit via the therapeutic gas inlet, and when the at least one bi-directional BCG flow sensor measures flow in the forward direction after the at least one bi-directional BCG flow sensor measures flow in the reverse direction, therapeutic gas is delivered into the breathing circuit after compensating for at least a portion of the flow in the reverse direction.

In one or more embodiments, compensating for at least a portion of the flow in the reverse direction comprises not delivering therapeutic gas into the breathing circuit until after an amount of forward flow has been measured equaling the reverse flow measured.

In one or more embodiments, compensating for at least a portion of the flow in the reverse direction comprises comparing the volume of the flow in the reverse direction to a dead space volume and not delivering therapeutic gas into the breathing circuit until after an amount of forward flow has been measured equaling the lesser of (i) the reverse flow measured or (ii) the dead space volume.

In one or more embodiments, information regarding the bi-directional BCG flow is used by the nitric oxide delivery system to ensure that a desired dose of NO is delivered into the injector module, and in turn into the breathing circuit.

In one or more embodiments, information regarding the bi-directional BCG flow is used by the nitric oxide delivery system to ensure that a desired dose of NO is not over delivered, overdosed, under delivered. and/or under dosed.

In one or more embodiments, the at least one bi-directional BCG flow sensor is a thermal mass flow meter.

In one or more embodiments, the at least one bi-directional BCG flow sensor measures flow without substantially interfering with flow in the patient breathing circuit.

In one or more embodiments, the at least one bi-directional BCG flow sensor has a substantially fast response time of less than about two milliseconds and provides a low resistance flow in the patient breathing circuit of less than about one hundred and fifty Pascals at about 60 standard liters per minute or about 1.5 cm H2O at about 60 standard liters per minute.

In one or more embodiments, the nitric oxide delivery system further comprises a carbon dioxide sensor that is one or more of (i) in fluid communication with the injector module and/or a connection between the breathing circuit and a sample line and (ii) is at and/or in the injector module and/or a connection between the breathing circuit and the sample line. In one or more embodiments, compensating for at least a portion of the flow in the reverse direction comprises delivering therapeutic gas into the breathing circuit for the reverse flow measured that contains carbon dioxide and not delivering therapeutic gas into the breathing circuit for the reverse flow measured that does not contain carbon dioxide.

In one or more embodiments, the bi-directional BCG flow sensor one or more of (i) has an operating range for forward flow that is greater than an operating range for reverse flow and (ii) has separate calibration data sets and/or calibration routines for forward and reverse flow.

Another aspect of the present invention relates to a nitric oxide delivery system comprising at least one sensor capable of measuring at least one characteristic of the breathing circuit gas. In one or more embodiments, the at least one characteristic is one or more of: (i) flow of the breathing circuit gas in a forward direction and in a reverse direction, (ii) a humidity of the breathing circuit gas, (iii) a temperature of the breathing circuit gas, and (iv) a type of gas in the breathing circuit gas. The nitric oxide delivery system can also comprise an injector module for delivering therapeutic gas into breathing gas in a breathing circuit, the injector module comprising: an injector body having a first opening and a second opening, the first opening and the second opening being configured to couple the injector module to a patient breathing circuit; and a therapeutic gas inlet configured to receive therapeutic gas and enable injection of the therapeutic gas into breathing circuit gas flowing through the injector module. The nitric oxide delivery system may also comprise a control module for providing the therapeutic gas to the therapeutic gas inlet. the control module being in communication with the at least sensor, and the control module compensating delivery of therapeutic gas and/or providing an alert based on the measurement from the at least one sensor.

In one or more embodiments, the at least one sensor is part of or in fluid communication with the injector module, and the control module provides an alert if the control module determines that the injector module is improperly placed in the breathing circuit.

In one or more embodiments, the at least one sensor is capable of measuring flow of the breathing circuit gas in a forward direction and in a reverse direction, and the control module determines that the injector module is improperly placed in the breathing circuit if the amount of reverse flow is greater than or equal to the amount of forward flow. In some embodiments, if the amount of revere flow is greater than the amount of forward flow, the control module determines that the injector module is placed in a reverse orientation and the control module compensates for such orientation by switching the measurements for reverse flow and forward flow.

In one or more embodiments, the at least one sensor is capable of measuring the humidity of the breathing circuit gas, and the control module determines that the injector module is improperly placed in the breathing circuit if the relative humidity of the breathing circuit gas is above 60%. In some embodiments, the at least one sensor comprises humidity sensor and/or a thermal conductivity sensor.

In one or more embodiments the at least one sensor is capable of measuring the temperature of the breathing circuit gas, and the control module determines that the injector module is improperly placed in the breathing circuit if the temperature of the breathing circuit gas is above 25° C. or is above 30° C.

In one or more embodiments, the at least one sensor is capable of measuring a type of gas in the breathing circuit gas, and the control module compensates delivery of therapeutic gas and/or provides an alert if the control module determines that the breathing circuit gas is not air or a mixture of air and oxygen.

In one or more embodiments, the at least one sensor is capable of measuring the type of gas by measuring a density of the breathing circuit gas and/or a thermal conductivity of the breathing circuit gas.

In one or more embodiments, the control module selects a new flow calibration curve if the control module determines that the breathing circuit gas is not air or a mixture of air and oxygen.

In one or more embodiments, the control module prompts a user to enter a gas type if the control module determines that the breathing circuit gas is not air or a mixture of air and oxygen.

In one or more embodiments, the control module alerts a user to raise a fresh gas flow rate at or above a patient's minute ventilation if the control module determines that the breathing circuit gas includes anesthesia gases and/or a user indicates that the breathing circuit gas includes anesthesia gases.

In one or more embodiments, the at least one sensor is part of or in fluid communication with the injector module, and the control module receives information indicative of and/or determines a ventilator type. In some embodiments, the control module determines the ventilator type based on information regarding the breathing gas.

In one or more embodiments, the control module determines the ventilator type is a BiPAP ventilator if the breathing circuit gas has one or more of (i) a low frequency and (ii) large volumes of reverse flow, and the control module one or more of (i) prompts a user to confirm the ventilator type, (ii) prompts a user to enter a dead space volume, (iii) prompts a user to add a carbon dioxide sensor to the breathing circuit, and (iv) prompts the user whether or not to compensate for a patient airway dead space.

In one or more embodiments, the control module determines the ventilator type is a HFOV ventilator if the breathing circuit gas has one or more of (i) a high frequency, (ii) low volumes of reverse flow, (iii) high frequency forward flow pulses, and (iv) high common mode pressure, and the control module one or more of (i) prompts a user to confirm the ventilator type and (ii) delivers therapeutic gas ratiometrically to an average flow measured by a BCG flow sensor.

In one or more embodiments, if the control module determines the ventilator type is a conventional ventilator, the control module one or more of (i) prompts a user to confirm the ventilator type and (ii) delivers therapeutic gas ratiometrically to the flow (e.g. instantaneous flow) measured by a BCG flow sensor.

In one or more embodiments, the control module determines the ventilator type by circuit pressure detection by using a gas injection tube in fluid communication with the therapeutic gas inlet as a pneumatic pressure sensing conduit.

In one or more embodiments, the at least one sensor comprises a carbon dioxide sensor. and the control module compensates for monitoring of the breathing circuit gas and/or therapeutic gas delivery based on the measurement from the carbon dioxide sensor.

BRIEF DESCRIPTION OF THE DRAWINGS

The features and advantages of the present invention will be more fully understood with reference to the following, detailed description when taken in conjunction with the accompanying figures, wherein.

DETAILED DESCRIPTION

The present invention generally relates to systems and method for delivery of therapeutic gas to patients, in need thereof, using at least enhanced breathing circuit gas (BCG) flow measurement. At least some of these enhanced BCG flow measurements can be used to address some phenomena that may, at times, occur when wild stream blending therapeutic gas into breathing gas that a patient receives from a breathing circuit affiliated with a ventilator. Utilizing at least some of these enhanced BCG flow measurements the dose of therapeutic gas wild stream blended into breathing gas that the patient receives from a ventilator can at least be more accurate and/or over delivery of therapeutic gas into the breathing gas can be avoided and/or reduced.

Systems and methods of the present invention can deliver therapeutic gas to a patient from a delivery system to an injector module, which in turn can be in fluid communication with a breathing circuit (affiliated with a ventilator) that the patient receives breathing gas from. Systems and methods of the present invention can include at least one BCG flow sensor that can measure the flow of patient breathing gas in the breathing circuit. Further, systems and methods of the present invention can deliver therapeutic gas into the breathing circuit such that the therapeutic gas wild stream blends with the patient breathing gas. Advantageously, the BCG flow sensor can measure flow in more than one direction (e.g., bi-directional BCG flow sensor) and/or address some of the phenomena that may, at times, occur when wild stream blending therapeutic gas into breathing gas in a breathing circuit affiliated with a frequency ventilator (e.g., high frequency ventilator, etc.).

Figure 1:
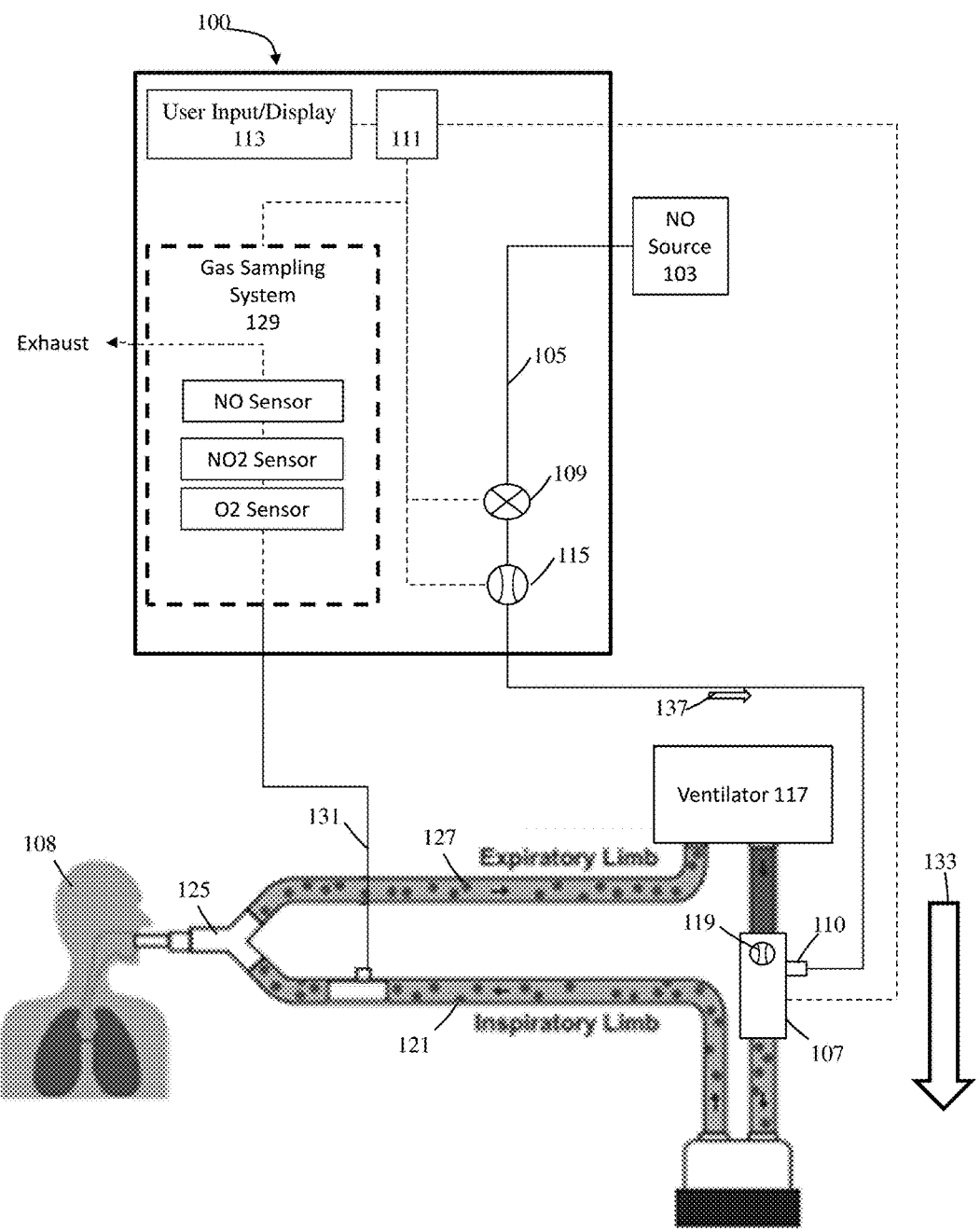
FIG. 1 illustratively depicts an exemplary nitric oxide delivery system, in accordance with exemplary embodiments of the present invention.

Referring to FIG. 1, illustratively depicted is an exemplary nitric oxide delivery system 100 for delivering therapeutic nitric oxide gas, via an injector module, to a patient receiving breathing gas from a ventilator. It will be understood that any teachings of the present invention can be used in any applicable system for delivering therapeutic gas to a patient receiving breathing gas from a breathing apparatus (e.g., ventilator. high frequency ventilator, breathing mask, nasal cannula, etc.). For example, systems and methods of the present invention can use, modify, and/or be affiliated with the delivery systems and/or other teachings of U.S. Pat. No. 5,558,083 entitled "Nitric Oxide Delivery System", the contents of which is incorporated herein by reference in its entirety.

Systems and methods of the present invention at times refer to use with a ventilator; however, systems and methods of the present invention can be used with any applicable breathing apparatus that may be affiliated with ventilation. Accordingly, reference to a ventilator is merely for ease and is in no way meant to be a limitation. The therapeutic gas, therapeutic gas wild stream blended into the breathing circuit, therapeutic gas delivery system, and the like are, at times, described with reference to nitric oxide gas (NO) used for inhaled nitric oxide gas therapy. It will be understood that other applicable therapeutic gases can be used. Accordingly reference to nitric oxide, NO, and the like is merely for ease and is in no way meant to be a limitation.

In exemplary embodiments, exemplary nitric oxide delivery systems such as nitric oxide delivery system 100 can be used to wild stream blend therapeutic gas (e.g., nitric oxide, NO, etc.) into patient breathing gas in a breathing circuit (affiliated with a ventilator) as a proportion of the patient breathing gas. To at least wild stream blend NO into patient breathing gas, nitric oxide delivery system 100 can include and/or receive nitric oxide from a nitric oxide source 103 (e.g., cylinder storing NO, NO generator. etc.) for example, via a conduit 105. Further, conduit 105 can also be in fluid communication with an injector module 107, for example, via a therapeutic gas inlet 110, and injector module 107 can also be in fluid communication with an inspiratory limb of a breathing circuit affiliated with a ventilator 117.

Figure 6A:
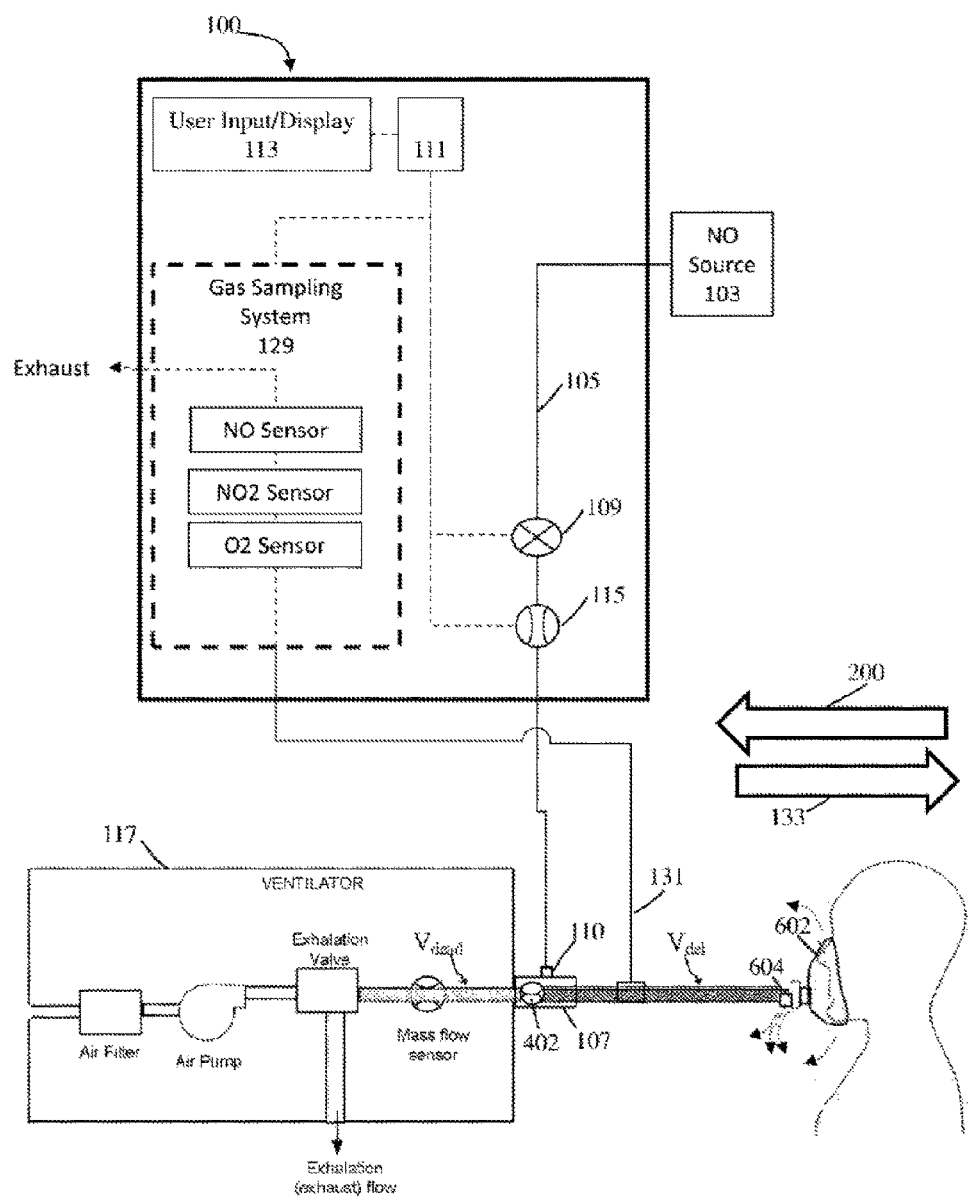
FIGS. 6A-6B illustratively depict an exemplary nitric oxide delivery system, in accordance with exemplary embodiments of the present invention.
Figure 6B:
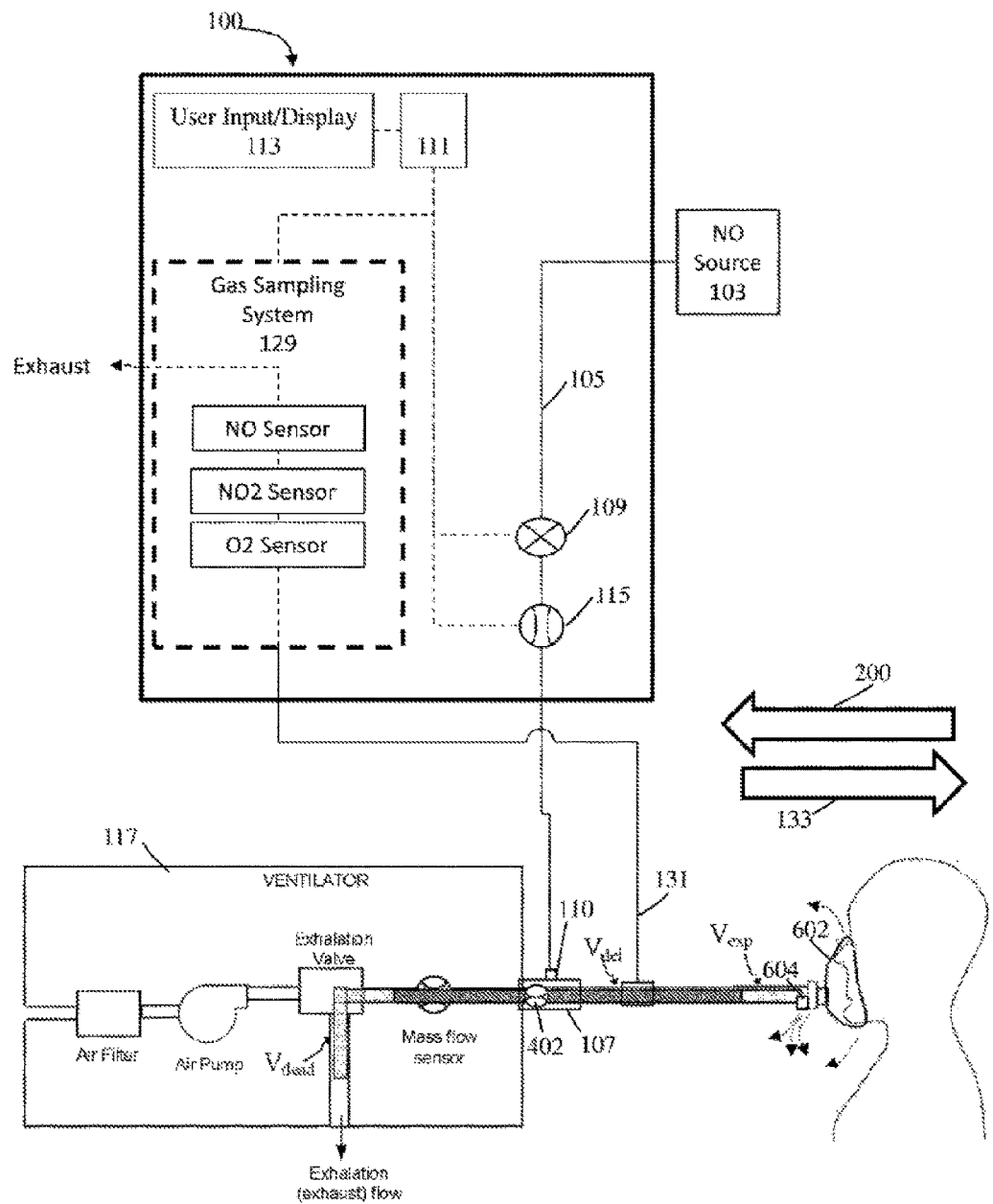

As shown, ventilator 117 can include an inspiratory outlet for delivering breathing gas (e.g., forward flow 133) to the patient via an inspiratory limb 121 and a "Y" piece 125 of a patient breathing circuit and an expiratory inlet for receiving patient expiration via an expiratory limb 127 and "Y" piece 125 of the patient breathing circuit. Generally speaking, this "Y" piece may couple inspiratory limb 121 and expiratory limb 127 and breathing gas being delivered and/or patient expiration may flow through the "Y" piece. At times, for ease, delivery and expiration of breathing gas is described without reference to the "Y" piece. This is merely for ease and is in no way meant to be a limitation. With injector module 107 coupled to inspiratory limb 121 of the breathing circuit and/or in fluid communication with the breathing circuit, nitric oxide can be delivered from nitric oxide delivery system 100 (e.g., NO forward flow 137) to injector module 107, via conduit 105 and/or therapeutic gas inlet 110. This nitric oxide can then be delivered, via injector module 107, into inspiratory limb 121 of the patient breathing circuit affiliated ventilator 117 being used to delivery breathing gas to a patient 108. In at least some instances, the patient breathing circuit can include only one limb for both inspiratory and expiratory flow. For example, as depicted in FIGS. 6A-6B, BiPAP ventilators can have only one limb that combines the inspiratory limb and expiratory limb. For ease, patient breathing circuits are, at times, depicted as having a separate inspiratory limb and expiratory limb. This is merely for ease and is in no way meant to be a limitation.

Referring back to FIG. 1, to regulate flow of nitric oxide through conduit 105 to injector module 107, and in turn to a patient 108 receiving breathing gas from the patient breathing circuit, nitric oxide delivery system 100 can include one or more control valves 109 (e.g., proportional valves, binary valves, etc.). For example, with control valve 109 open, nitric oxide can be delivered to patient 108 by flowing in a forward direction (e.g., NO forward flow 137) through conduit 105 to injector module 107, and in turn to patient 108.

In at least some instances, nitric oxide delivery system 100 can include one or more NO flow sensors 115 that can measure the flow of therapeutic gas (e.g., NO forward flow 137) through control valve 109 and/or conduit 105, in turn enabling measurement of the flow of therapeutic gas through a therapeutic gas inlet 110 into injector module 107, and in turn to patient 108. Further, in at least some instances, injector module 107 can include one or more breathing circuit gas (BCG) flow sensors 119 that can measure the flow of at least patient breathing gas (e.g., forward flow 133) through injector module 107, and in turn to patient 108. Although shown as being at injector module 107, BCG flow sensor 119 can be placed elsewhere in the inspiratory limb 121, such as upstream of the injector module 107 and/or in fluid communication with the breathing circuit. Also, instead of receiving flow information from BCG flow sensor 119, nitric oxide delivery system 100 may receive flow information directly from the ventilator 117 indicating the flow of breathing gas from ventilator 117.

In exemplary embodiments, nitric oxide gas flow can be wild stream blended proportional (also known as ratiometric) with the breathing gas flow to provide a desired concentration of NO in the combined breathing gas and therapeutic gas. For example, nitric oxide delivery system 100 can confirm that the desired concentration of NO is in the combined breathing gas and therapeutic gas by using the known NO concentration of NO source 103; the amount of breathing gas flow in the patient circuit using information from BCG flow sensor 119; and the amount of therapeutic gas flow in conduit 105 to injector module 107 (and in turn to patient 108) using information from NO flow sensor 115.

To at least deliver desired set doses of therapeutic gas to a patient and/or sample therapeutic gas being delivered to a patient, nitric oxide delivery system 100 can include a system controller 111 that may comprise one or more processors and memory, where the system controller may be for example a computer system, a single board computer, one or more application-specific integrated circuits (ASICs), or a combination thereof. Processors can be coupled to memory and may be one or more of readily available memory such as random access memory (RAM), read only memory (ROM), flash memory, compact/optical disc storage, hard disk, or any other form of local or remote digital storage. Support circuits can be coupled to processors, to support processors, sensors, valves, sampling systems, delivery systems, user inputs, displays, injector modules, breathing apparatus, etc. in a conventional manner. These circuits can include cache memory, power supplies, clock circuits, input/output circuitry, analog-to-digital and/or digital-to-analog convertors, subsystems, power controllers, signal conditioners, and the like. Processors and/or memory can be in communication with sensors, valves, sampling systems, delivery systems, user inputs, displays, injector modules, breathing apparatus, etc. Communication to and from the system controller may be over a communication path, where the communication path may be wired or wireless, and wherein suitable hardware, firmware, and/or software may be configured to interconnect components and/or provide electrical communications over the communication path(s).

The clock circuits may be internal to the system controller and/or provide a measure of time relative to an initial start, for example on boot-up. The system may comprise a real-time clock (RTC) that provides actual time, which may be synchronized with a time-keeping source, for example a network. The memory may be configured to receive and store values for calculations and/or comparison to other values, for example from sensor(s), pumps, valves, etc.

In exemplary embodiments, the memory may store a set of machine-executable instructions (or algorithms), when executed by processors, that can cause the sampling system and/or delivery system to perform various methods and operations. For example, the delivery system can perform a method to, for example. deliver a desired set dose of therapeutic gas (e.g., NO concentration, NO PPM, etc.) to a patient in need thereof comprising: receiving and/or determining a desired set dose of therapeutic gas to be delivered to a patient, for example, that may be input by a user; measuring flow in the inspiratory limb of a patient breathing circuit; delivering therapeutic gas containing NO to the patient during inspiratory flow; monitoring inspiratory flow or changes in the inspiratory flow; and varying the quantity (e.g. volume or mass) of therapeutic gas delivered in a subsequent inspiratory flow.

For another example, the sampling system can perform a method to, for example, determine the concentration of target gas (e.g., NO) being delivered to a patient comprising: actuating a sampling pump and/or opening a gas sampling valve (e.g., three way valve, etc.) to obtain a gas sample from the inspiratory limb of a patient breathing circuit, the gas sample being of blended air and therapeutic gas (e.g., NO) being delivered to a patient; exposing the gas sample to gas sensors (e.g., catalytic type electrochemical gas sensors); obtaining information from the sensor indicative of the concentration of target gas (e.g., NO, nitrogen dioxide, oxygen) being delivered to the patient; communicating to the user the concentration of the target gas. The machine-executable instructions may also comprise instructions for any of the other methods described herein.

Further, to at least ensure accurate dosing of the therapeutic gas, nitric oxide delivery system 100 can include a user input/display 113 that can include a display and a keyboard and/or buttons, or may be a touchscreen device. User input/display 113 can receive desired settings from the user, such as the patient's prescription (in mg/kg ideal body weight, mg/kg/hr, mg/kg/breath, mL/breath, cylinder concentration, delivery concentration, duration, etc.), the patient's age, height, sex, weight, etc. User input/display 113 can in at least some instances be used to confirm patient dosing and/or gas measurements, for example, using a gas sampling system 129 that can receive samples of the gas being delivered to patient 108 via a sample line 131. Gas sampling system 129 can include numerous sensors such as, but not limited to, nitric oxide gas sensors, nitrogen dioxide gas sensors, and/or oxygen gas sensors, to name a few that can be used to display relevant information (e.g., gas concentrations, etc.) on user input/display 113.

Although the above can be used beneficially to deliver therapeutic gas to a patient receiving breathing gas from a patient breathing circuit affiliated with a ventilator, wild stream blending of NO into patient breathing gas as a percentage of the patient breathing gas can fail to account for at least some surprising phenomena applicant discovered. Without knowledge of at least some of these phenomena the actual NO concentration (e.g., NO as a concentration of the patient breathing gas. Parts Per Million (PPM) NO, etc.) can be different from the desired NO percentage. For example, these surprising phenomena may, at times, cause and/or be affiliated with the actual NO percentage being higher than the desired NO percentage. This NO percentage can be particularly important as delivery of dosing to a patient that may not be the desired therapeutic dose may impact efficacy. Accordingly, by taking into account at least some of these surprising phenomena more accurate NO dosing can be possible.

Figure 2:
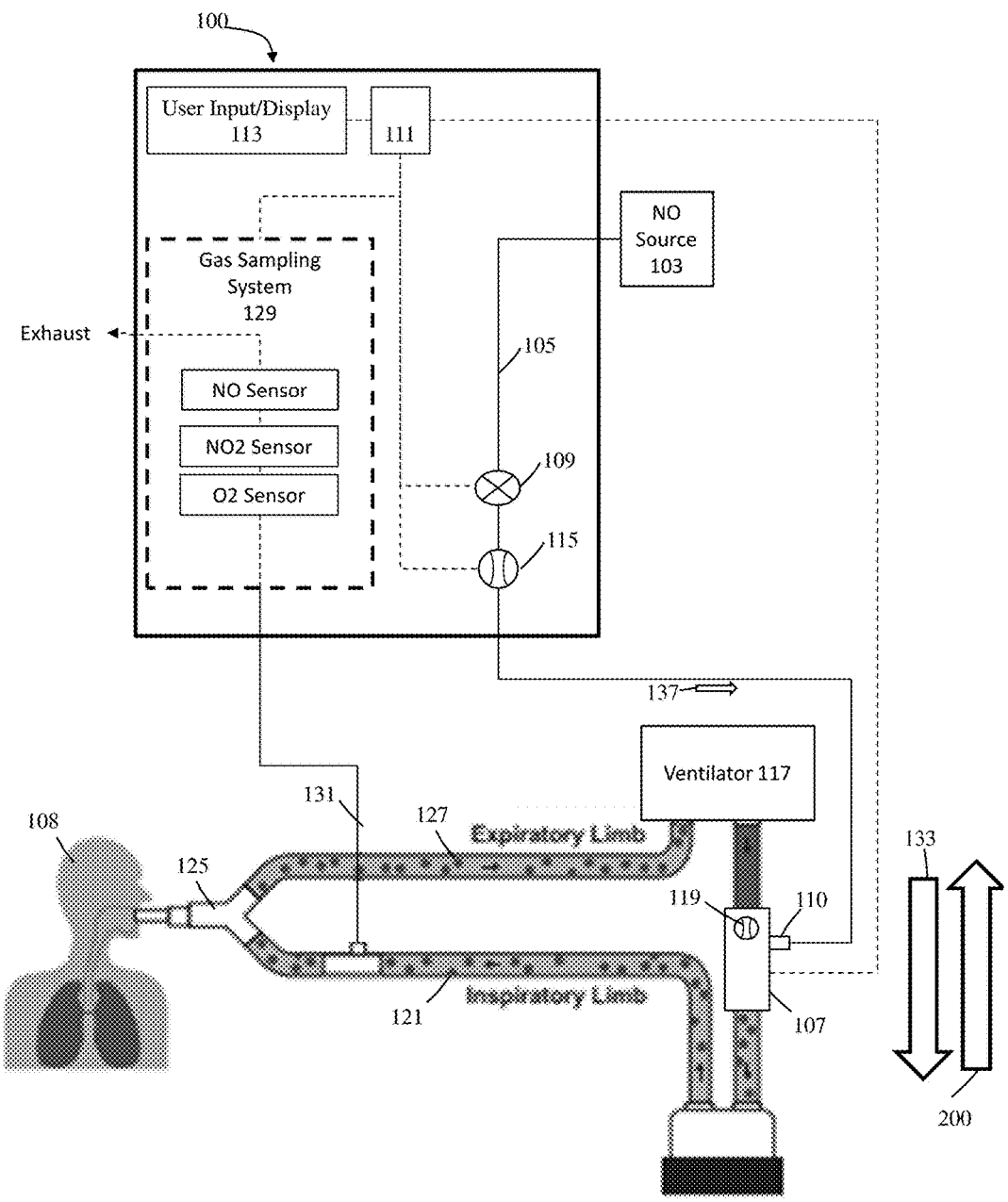
FIG. 2 illustratively depicts an exemplary nitric oxide delivery system and/or forward and reverse flowing patient breathing gas in a patient breathing circuit, in accordance with exemplary embodiments of the present invention.

Extensive study discovered a surprising phenomenon (reverse breathing circuit gas (BCG) flow phenomenon) where, it was surprisingly found that, at times, the flow of gas (e.g., patient breathing gas, therapeutic gas, combined patient breathing gas and therapeutic gas, etc.) in the breathing circuit can actually be in directions other than the forward direction. For example, referring to FIG. 2, the flow of gas in the breathing circuit can be in the forward direction (e.g., forward flow 133) from ventilator 117 towards the patient and, at times, surprisingly, the flow of gas in the breathing circuit can be in a reverse direction (e.g., reverse flow 200) away from the patient towards ventilator 117. This flow in the reverse direction (e.g., reverse flow 200) can be caused by numerous sources, such as, but not limited to, reverse flow caused by valves (not shown) in ventilator 117 rapidly actuating (e.g., closing); flow driven by the patient (e.g., the patient spontaneously breathing); reverse flow during at least the first part of the patient's exhalation phase, for example, when using single limb circuits such as those used with BiPAP Ventilators; and/or a blockage of the expiratory limb; to name a few. The above described bi-directional flow in the breathing circuit can result in numerous problems, such as overdosing of therapeutic gas into the patient breathing circuit.

Reverse flow can be problematic for nitric oxide delivery system 100 as therapeutic gas, generally speaking, is delivered into breathing gas, via injector module 107, based on BCG flow sensor 119 measuring one way flow of breathing gas flowing from ventilator 117. As BCG flow sensor 119 cannot determine flow direction, flow in reverse direction may be reported as forward flow. (i.e., in the forward flow 133 direction from ventilator 117 towards patient 108), nitric oxide delivery system 100 can deliver undesirable higher doses than the desired doses (e.g., desired set doses, etc.) of therapeutic gas into the breathing gas when this reverse flow phenomenon occurs. Failure to detect and/or compensate for at least the above phenomena may, at times, lead to delivery of dosing to a patient that may not be the desired therapeutic dose and, this may, at times, impact efficacy and/or may result in an alarm (e.g., a delivery failure alarm condition, etc.).

By way of example, when breathing gas flow in the forward direction is measured by BCG flow sensor 119, nitric oxide delivery system 100 can deliver therapeutic gas into the forward flowing breathing gas via injection module 107; however, since BCG flow sensor 119 cannot detect flow in a direction other than the forward direction it may not differentiate between no flow and flow in the reverse direction. Following the above example, if after flowing in the forward direction the combined therapeutic gas and breathing gas then flows in the reverse direction, BCG flow sensor 119 may view this as zero flow ending delivery of the therapeutic gas into the breathing gas (which actually may be breathing gas with therapeutic gas). This breathing gas and therapeutic gas mixture can then revert back to flowing in the forward direction, which BCG flow sensor 119 can measure so nitric oxide delivery system 100 may then over-deliver therapeutic gas into the forward flowing breathing gas and therapeutic gas mixture via injection module 107. This can lead to a double dose of therapeutic gas in the breathing gas as the breathing gas would receive an initial injection of therapeutic gas when first detected flowing in the forward direction and then would receive another injection of therapeutic gas when the combined therapeutic gas (initial injection) and breathing gas again flows in the forward direction. Accordingly, the patient may then receive breathing gas with twice the desired dose of therapeutic gas.

By way of another example, if BCG flow sensor 119 is unable to differentiate the direction of flow and reads flow in the forward and reverse direction as being the same then the patient may receive a triple dose of therapeutic gas. For example, when flow (e.g., breathing gas flow) in the forward direction is measured by BCG flow sensor 119, nitric oxide delivery system 100 may deliver a first dose of therapeutic gas into the forward flowing breathing gas via injection module 107. If this breathing gas and therapeutic gas mixture then flows in the reverse direction, when measured by BCG flow sensor 119, nitric oxide delivery system 100 can then delivery a second dose of therapeutic gas into the reverse flowing breathing gas and therapeutic gas mixture resulting in the breathing gas having twice the desired dose of therapeutic gas. Further, if this breathing gas and double dose of therapeutic gas mixture then flows in the forward direction, when measured by BCG flow sensor 119, nitric oxide delivery system 100 may yet again deliver a third dose of therapeutic gas into the forward flowing breathing gas and double dose of therapeutic gas mixture resulting in the breathing gas having three times the desired dose of therapeutic gas. Accordingly, the patient may then receive breathing gas with three times the desired dose of therapeutic gas.

Figure 3:
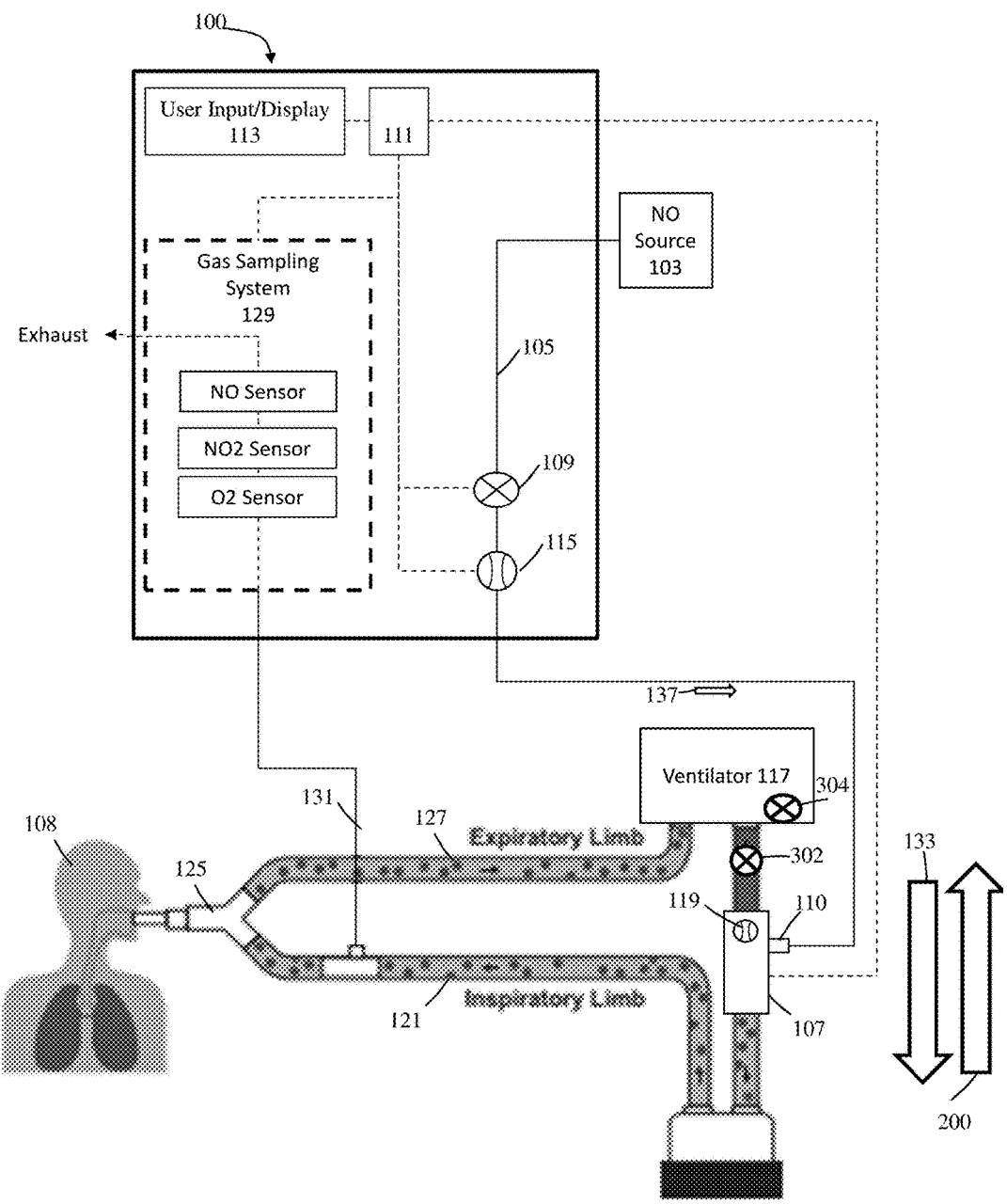
FIG. 3 illustratively depicts an exemplary nitric oxide delivery system including a check valve and/or free breathing valve, in accordance with exemplary embodiments of the present invention.

Referring to FIG. 3, in exemplary embodiments, addressing at least reverse BCG flow, a check valve 302 (e.g., a pneumatic check valve) can be placed in fluid communication with inspiratory limb 121. For example, check valve 302 can be placed at inspiratory limb 121 upstream of injector module 107. In use, check valve 302 can open so reverse BCG flow (e.g., reverse flow 200), vibrations, etc. can be diverted prior to being measured by BCG flow sensor 119. Although the use of check valves can address at least some of the issues affiliated with reverse BCG flow, these check valves can also introduce numerous problems such as, but not limited to. response flow lag from forward flow cracking pressure, surface seal and material electrostatic physical attraction to contamination affecting seal performance, unit to unit repeatability from component tolerance or material choice, surface finish affecting seal performance, characterized as an un-damped spring mass system vulnerable to producing audible noise or forward flow inducing oscillation "noise", and/or can detract from the overall flow control accuracy, repeatability, and control response time, to name a few.

Further, check valve 302 can interfere with ventilators that include a free breathing valve 304. Free breathing valve 304 (sometimes called an anti-suffocation valve) can open to atmosphere should the ventilator fail, a blockage occur in the breathing circuit, and/or a patient using the ventilator spontaneously breath. Free breathing valve 304 can be required for ventilators to ensure that a patient who attempts to spontaneously breathe has the ability to inhale air. By way of example, if a ventilator does not include this free breathing valve it can be considered as a closed system with the ventilator being in control of when breathing air can be delivered to the patient. Without this free breathing valve, if a patient attempts to spontaneously breathe the user can be unable to pull in air to breathe as there can be no entrance for air to flow into the patient breathing circuit. With this free breathing valve, if a patient attempts to spontaneously breathe then the free breathing valve actuates enabling the user to pull in air from the surrounding environment. For ventilators that include free breathing valves, check valves included in the patient breathing circuit may only allow for inhalation from the free-breathing valve and not exhalation as the check valve can defeat the purpose of this safety feature and may not be used with such ventilators.

Similar to a free-breathing valve, a mechanical over-pressure relief valve may be connected to the inspiratory limb of the breathing circuit, alone or in combination with the free breathing valve, and at least the mechanical over-pressure relieve valve may be utilized as a redundant safety measure to relieve airway pressure in the event of ventilator exhalation valve failure, blockage, and/or expiratory limb circuit blockage. The check valve used for preventing reverse flow in series with inspiratory limb can prevent over-pressure reverse flow gas from escaping to atmosphere.

There can also be other issues affiliated with using check valves. For example, check valves can, at times, present training and/or usability issues (e.g., check valves may be used when not needed, check valves may be omitted when needed, etc.). It may also be difficult to disconnect and/or disassembly the breathing circuit to insert the check valve and/or numerous adaptors may be required to couple check valves with breathing circuits.

In exemplary embodiments, to reduce and/or prevent at least interference with free breathing valve 304, check valve 302 and/or an additional check valve can be placed at injector module 107, therapeutic gas inlet 110, and/or conduit 105.

Figure 4A:
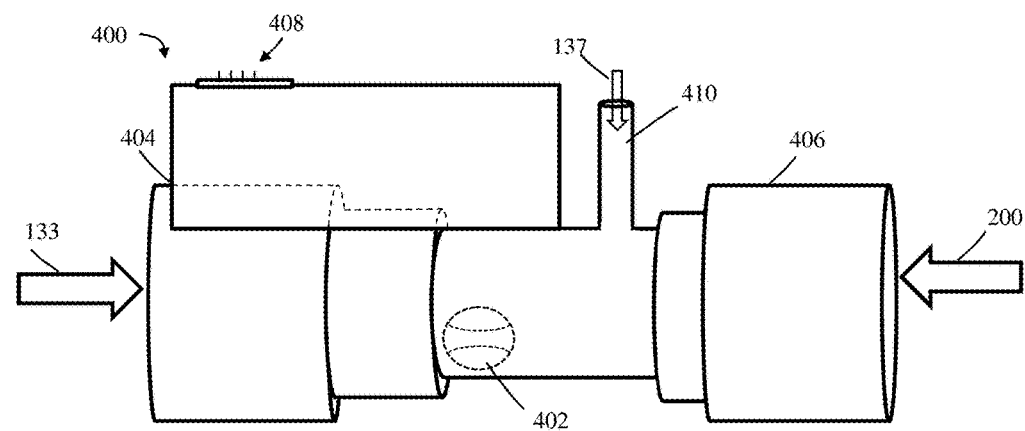
FIGS. 4A-4B illustratively depict an exemplary injector module that includes a bi-directional BCG flow sensor, in accordance with exemplary embodiments of the present invention.
Figure 4B:
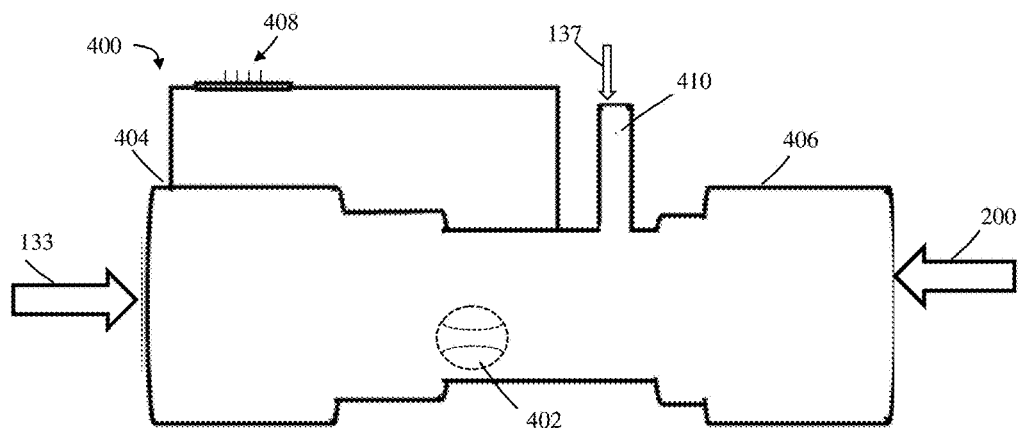

Referring to FIGS. 4A-4B, exemplary injector modules (e.g., injector module 400) that can include, and/or that can be in fluid communication with, at least one bi-directional flow sensor (e.g., bi-directional BCG flow sensor 402) are illustratively depicted that can at least address some of the above phenomena (e.g., reverse BCG flow, etc.) and/or that can provide additional benefits. Injector module 400 can include a first end 404 and second end 406 that can be coupled to the inspiratory limb of the patient breathing circuit and/or in can be in fluid communication with the patient breathing circuit. At first end 404 and second end 406 there can be a first opening and second opening, respectively, in the body of injector module 400 enabling fluid flow (e.g., breathing gas, etc.) through the injector module. Injector module 400 can also include a communication port 408 enabling communication of information between the injector module (and any affiliated components) and the nitric oxide delivery system. In at least some instances, communication port 408 and/or another communications port can be in fluid communication with nitric oxide delivery system and/or a pressure sensor (e.g., differential pressure sensor(s), differential pressure sensor(s) used for measuring flow, pressure sensor for determining common mode pressure in the breathing circuit, etc.). Further, injector module 400 can include a therapeutic gas inlet 410 that can receive therapeutic gas from the nitric oxide delivery system and/or can enable injection of therapeutic gas into breathing gas flowing through the injector module. In at least some instances, therapeutic gas inlet 410 can be in fluid communication with a pressure sensor(s) or other relevant sensor(s) affiliated with the delivery device and/or can provide a pneumatic conduit for reporting breathing circuit airway pressure, common mode pressure for determination of ventilation application. In at least some instance, the bi-directional flow information can be received via communication (e.g., direct communication, indirect communication, etc.) from the ventilator.

In exemplary embodiments, addressing at least reverse flow, injector module 400 can include and/or be in fluid communication with an at least one bi-directional BCG flow sensor 402 capable of measuring bi-directional flow of breathing gas in the patient breathing circuit. With injector module 400 in fluid communication with the inspiratory limb of the patient breathing circuit, bi-directional BCG flow sensor 402 can measure bi-directional flow within the inspiratory limb of the breathing circuit so that therapeutic gas (e.g., from the nitric oxide delivery system) can be delivered into the breathing gas when bi-directional BCG flow sensor 402 measures forward flow 133 and/or therapeutic gas may not be delivered into the breathing gas when bi-directional BCG flow sensor 402 measures reverse flow 200. Using injector module 400, bi-directional BCG flow sensor 402, and the nitric oxide delivery system in at least this manner can eliminate the above described scenario of overdosing (e.g., double dosing, triple dosing, etc.) of therapeutic gases being delivered to the patient using a ventilator and/or ventilator application which may cause periods of reverse flow. This can ensure the patient receives breathing gas mixed with the desired dosing of therapeutic gas.

In exemplary embodiments, bi-directional BCG flow sensor 402 can be any sensor capable of measuring flow in both the forward and reverse direction without substantially interfering with flow and/or pressure in the patient breathing circuit (e.g., as flow and/or pressure in the breathing circuit can be extremely precise and important for treating the patient) and that provides a substantially fast response time (e.g., enabling substantially fast communication of flow information to the nitric oxide delivery system). For example, bi-directional BCG flow sensor 402 can be a thermal mass flow meter (sometimes called a thermal dispersion flow meter); pressure-based flow meter; optical flow meter; electromagnetic, ultrasonic, and/or Coriolis flow meter; laser Doppler flow meter, and/or any flow meter that provides a response time of less than about two milliseconds and that provides a low resistance of less than about one hundred and fifty Pascals at about 60 standard liters per minute (SLPM) and/or about 1.5 cm $H_2O$ at about 60 standard liters per minute.

Further to the above difficulties, measuring both forward and reverse flow can be substantially difficult, for example, because, the accuracy of the flow measurements can effect dosing of the therapeutic gas delivered to the patient, measurement of flow in at least the reverse direction may not compromise measurement ranges and accuracy of flow in the forward direction, flow (e.g., peak flow) in the forward direction can be much larger than flow in the reverse direction, and/or flow calibration curve and/or outputs may be differ for forward and reverse flow, to name a few. In exemplary embodiments, the bi-directional flow sensor may measure from −50 SLPM (e.g., 50 SLPM flow in the reverse direction) to about +180 SLPM (e.g., 180 SLPM flow in the forward direction). At least some of these difficulties may be even further compounded as there may be NO injection ports and/or other features downstream of the flow sensor that may impact flow measurement accuracy of at least BCG flow, for example, when flowing in at least the reverse direction.

In exemplary embodiments, bi-directional BCG flow sensor 402 can be in communication with the nitric oxide delivery system via communication port 408. This can allow flow information to be communicated to the nitric oxide delivery system, which can be used by the nitric oxide delivery system for NO delivery and/or monitoring. Using this bi-directional flow information the nitric oxide delivery system can more accurately deliver and/or monitor NO.

Figure 5:
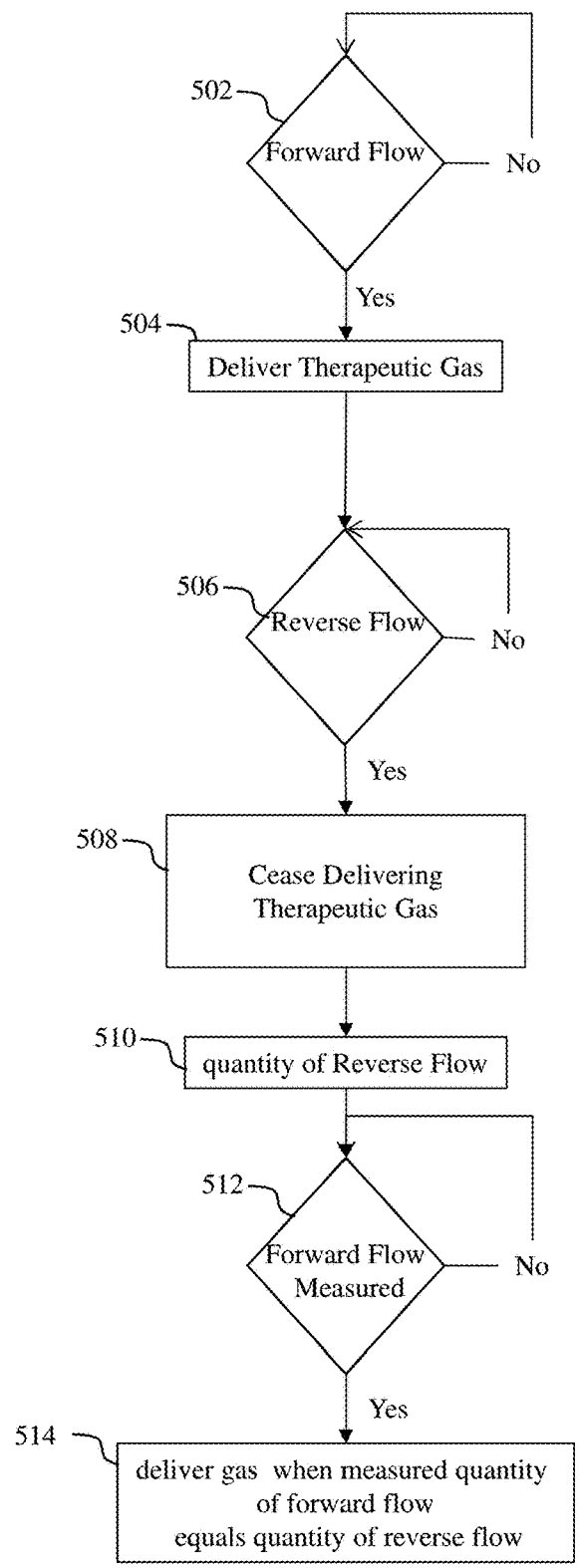
FIG. 5 illustratively depicts an algorithm for compensating for reverse flow and/or avoiding over delivery of therapeutic gas, in accordance with exemplary embodiments of the present invention.

Referring to FIG. 5, in exemplary embodiments, with the injector module including and/or being in fluid communication with a bi-directional BCG flow sensor, nitric oxide delivery system (e.g., using CPU 111) can include a therapeutic gas delivery algorithm that delivers therapeutic gas when forward flow is, for example, measured after compensating for previously measured reverse flow. By way of example, when the bi-directional flow sensor measures forward flow, at step 502, then the nitric oxide delivery system (e.g., using CPU 111) can deliver therapeutic gas to the injector module, and in turn into the patient breathing circuit (e.g., in a proportional amount to achieve a constant therapeutic gas concentration) at step 504. This process can be repeated for later measured forward flows. However, if the bi-directional flow sensor measures reverse flow, at step 506, then the nitric oxide delivery system (e.g., using CPU 111) may not deliver and/or may stop delivery of the therapeutic gas, at step 508.

The volumetric quantity of reverse flow can then be determined, at step 510, for example, by nitric oxide delivery system (e.g., using CPU 111) using flow information from the bi-directional flow sensor. Continuing the above example, at step 512, the bi-directional flow sensor can again measure forward flow (e.g., after measuring bi-directional flow) then, at step 514, the nitric oxide delivery system (e.g., using CPU 111) can deliver the therapeutic gas into the forward flow stream after an amount of forward flow has been measured equaling the totalized volume of reverse flow measured.

Following the above example, in exemplary embodiments, by not delivering the therapeutic gas until all the reverse flow that passed through the injector module has forward flowed passing again through the injector module, the therapeutic gas may not be double dosed. For example, when the bi-directional flow sensor measured forward flow, at step 512, had the nitric oxide delivery system (e.g., using CPU 111) begun delivering the therapeutic gas into the forward flow stream immediately (e.g., without waiting for the reverse flow to pass) the reverse flow that begun flowing forward would be double dosed.

In exemplary embodiments, the nitric oxide delivery system can be used with a BiPAP ventilator, which is affiliated with a breathing circuit having a single limb rather than an inspiratory limb and a separate expiratory limb. Such an arrangement provides unique challenges and considerations, as will be further detailed below.

Referring to FIG. 6A, in exemplary embodiments the patient receives breathing gas from a ventilator 117, such as a BiPAP ventilator. The systems and methods described may be used with any breathing apparatus that utilizes a single limb for inspiratory and expiratory flow and/or any breathing apparatus that utilizes an exhalation valve (also known as a pressure regulation valve) upstream of the one or more BCG flow sensors. In at least some instances the breathing apparatus can include breathing mask 602 and/or an exhaust port 604. Further, in at least some instances, BiPAP ventilator can include a bias flow rate that can be substantially high (e.g., more than 10 liters per minute. 10-20 liters per minute, etc.) that may be used to expel expiratory flow (e.g., from the patient) out of exhaust port 604 and/or leaking about the mask (e.g., during expiration, during inspiration, etc.).

Due at least in part to the single limb in the breathing circuit, the one or more bi-directional BCG flow sensors 402 experience significant forward and reverse flow to and from the patient. When the BCG flow sensors measure forward flow 133 of breathing gas, therapeutic gas is delivered to the breathing gas, such as via therapeutic gas inlet 110. The therapeutic gas-containing breathing gas then travels along the single limb towards the patient. Thus, the breathing gas between the therapeutic gas inlet 110 and the patient has undergone therapeutic gas delivery, and the volume of such breathing gas is designated as $V_{del}$ in FIG. 6A. As the therapeutic gas inlet 110 can be located in close proximity to the bi-directional BCG flow sensor 402 (i.e. the distance from bi-directional BCG flow sensor 402 to therapeutic gas inlet 110 can be much less than the distance between the therapeutic gas inlet 110 and the patient), $V_{del}$ can also be approximated as the volume of breathing gas in the breathing circuit between the bi-directional BCG flow sensor 402 and the patient. $V_{del}$ may be a known parameter that is input by the user, or may be determined by the nitric oxide delivery system 100.

The breathing circuit in FIG. 6A also includes an exhalation valve to allow expiratory flow from the patient to be exhausted, as the breathing circuit does not include a separate expiratory limb. The volume of breathing circuit between the bi-directional BCG flow sensor 402 and the exhalation valve is designated as dead space volume V dead. V dead may be a known parameter that is input by the user, or may be determined by the nitric oxide delivery system 100. For example, the user may select and/or enter information affiliated with a specific ventilator and/or ventilator type (e.g., using a user interface affiliated with the therapeutic gas delivery system) and the appropriate $V_{dead}$ can be applied because, for example, the gas delivery system can store and/or access various $V_{dead}$ values correlated to specific ventilators. The appropriate value for $V_{dead}$ can then be applied. In at least some instances, the therapeutic gas delivery system may detect significant quantities of reverse flow volume (e.g., greater than 100 ml, etc.) at relatively low frequencies (e.g. <0.5 Hz), and significantly less net reverse flow volume than forward flow volume (e.g. at least a 2:1 ratio of forward to reverse flow) and may prompt the user to enter the $V_{dead}$ value and/or select and/or enter information affiliated with the specific ventilator and/or ventilator type. In at least some instance, information (e.g., $V_{dead}$, etc.) can be communicated and/or retrieved from the ventilator.

Now referring to FIG. 6B, during the patient's exhalation phase, the patient introduces an expiratory volume $V_{exp}$ into the breathing circuit. $V_{exp}$ then displaces at least a portion of $V_{del}$ which in turn displaces at least a portion of $V_{dead}$. Some or all of this displaced $V_{dead}$ can be exhausted to the environment through the exhalation valve. This displacement of breathing gas in reverse direction can be measured as reverse flow 200 if the BCG flow sensor(s) are bi-directional BCG flow sensors 402. This reverse flow may be compensated for according to the methods described above. In at least some instances, the NO delivery system may prompt users to add a segment of tubing to the single limb breathing circuit ensuring that the relative volumes of reverse flow and $V_{dead}$ are such that reverse flow may be compensated according to the methods above (e.g. ensuring $V_{exp}$ is less than $V_{del}$, etc.). In at least some instances, $V_{dead}$ may be substantially small (e.g. <25 ml) and may be substantially insignificant such that compensation can be 0 ml. For example, the NO delivery system may not deliver during reverse flow instances and/or may deliver during forward flow. However, depending on the relative volumes of $V_{del}$, $V_{dead}$ and $V_{exp}$, some of breathing gas containing therapeutic gas ($V_{del}$) may be exhausted through the exhalation valve. Accordingly, in exemplary embodiments, some or all of the reverse flow is compensated for, depending on the relative volumes of $V_{del}$, $V_{dead}$ and $V_{exp}$.

Figure 7:
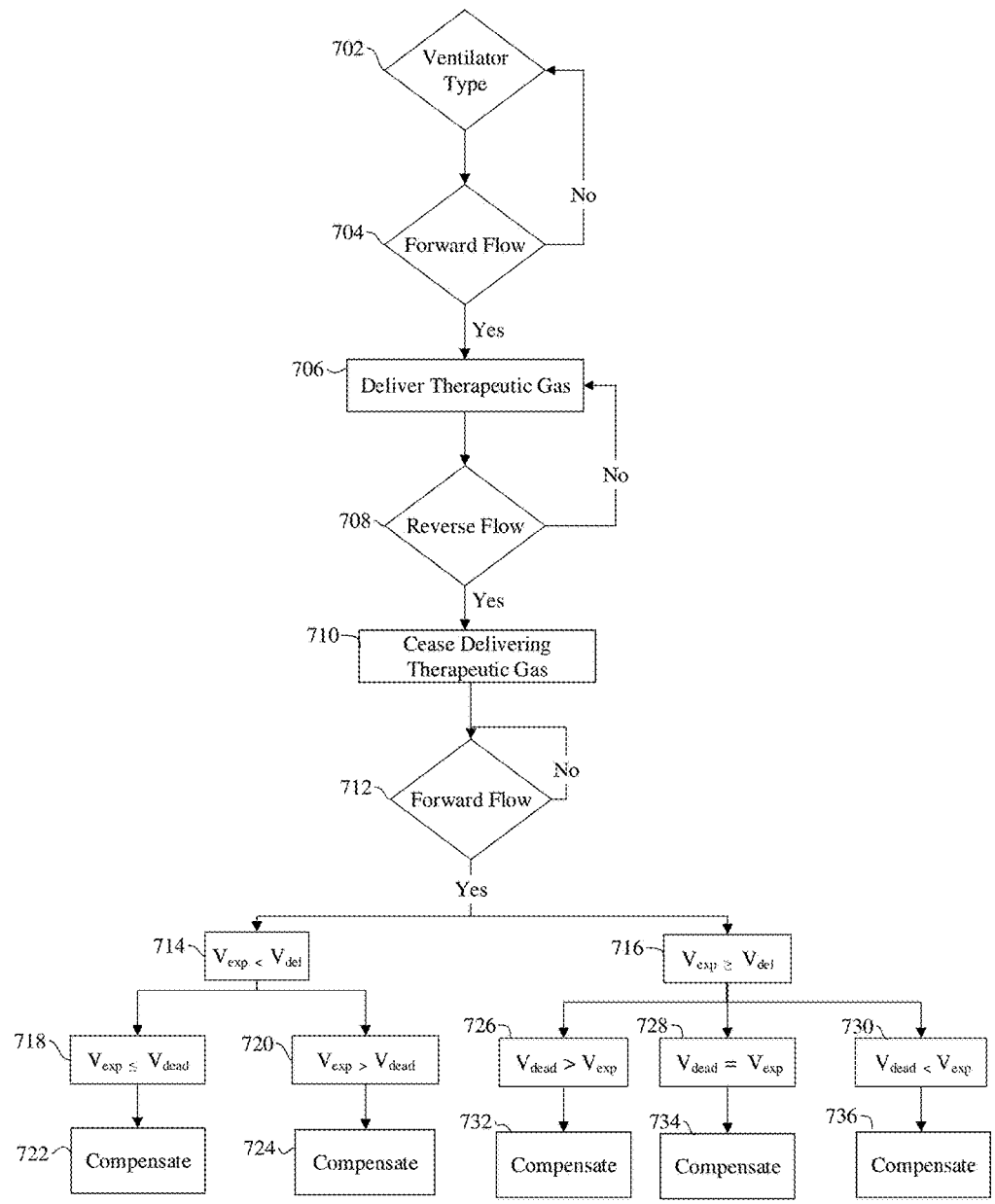
FIG. 7 illustratively depicts an algorithm for compensating for reverse flow and/or avoiding over delivery of therapeutic gas, in accordance with exemplary embodiments of the present invention.

Referring to FIG. 7, in exemplary embodiments, with the injector module including and/or being in fluid communication with a bi-directional BCG flow sensor, nitric oxide delivery system (e.g., using CPU 111) can include a therapeutic gas delivery algorithm that delivers therapeutic gas when forward flow is, for example, measured after compensating for at least a portion of the previously measured reverse flow. By way of example, at step 702, the type of ventilator (e.g. BiPAP, high frequency ventilator, constant flow ventilator, variable flow ventilator, etc.) can be input by the user, or may be determined by the nitric oxide delivery system (e.g., using CPU 111) based on flow information from the bi-directional flow sensor. For example, small volumes of reverse flow detected at high frequencies may be indicative of a high frequency ventilation application. Detection of high common mode pressure in the breathing circuit would confirm a high frequency ventilation application. As another example, larger volumes of reverse flow (e.g. on the same order of magnitude as the volumes of forward flow) may be indicative of a BiPAP ventilator. By way of example, small, transient periods of zero flow, reverse flow, and/or continuous forward bias flow volume (e.g., less than 100 ml, etc.) at low frequencies (e.g., less than 1 hertz, less than 1 breath per minute. etc.) can be indicative of a conventional ventilator.

If the ventilator type is a BiPAP ventilator or similar ventilator, then the algorithm can proceed with the steps as indicated in FIG. 7. If the ventilator type is not a BiPAP ventilator or similar ventilator, then the algorithm can include the steps in FIG. 5 above. However, it is also possible to perform the steps in FIG. 7 with ventilator types other than BiPAP ventilators, with the assumption that the dead space volume is infinitely large (i.e. $V_{dead}$ is always» $V_{exp}$).

When the bi-directional flow sensor measures forward flow, at step 704, then the nitric oxide delivery system (e.g., using CPU 111) can deliver therapeutic gas to the injector module, and in turn into the patient breathing circuit (e.g., in a proportional amount to achieve a constant therapeutic gas concentration) at step 706. This process can be repeated for later measured forward flows, such as in step 712. However, if the bi-directional flow sensor measures reverse flow, at step 708, then the nitric oxide delivery system (e.g., using CPU 111) may not deliver and/or may stop delivery of the therapeutic gas, at step 710.

The volumetric quantity of reverse flow can then be determined, for example, by nitric oxide delivery system (e.g., using CPU 111) using flow information from the bi-directional flow sensor. However, depending on the relative volumes of $V_{del}$, $V_{dead}$ and $V_{exp}$, only a portion of the reverse flow may be compensated for.

As an example, if $V_{exp}<V_{del}$ as set forth in step 714, then $V_{dead}$ can serve as an upper limit for the amount of reverse flow to be compensated. That is, if $V_{exp}\, V_{dead}$ as set forth in step 718, then the entire reverse flow ($V_{exp}$) is compensated for as set forth in step 722, e.g. the nitric oxide delivery system (e.g., using CPU 111) can deliver the therapeutic gas into the forward flow stream after an amount of forward flow has been measured equaling the totalized volume of reverse flow measured. If $V_{exp}>V_{dead}$ as set forth in step 720, then some portion of $V_{del}$ may be lost through the exhalation valve, and thus $V_{dead}$ is the upper limit for compensation as set forth in step 724. Accordingly, the nitric oxide delivery system (e.g., using CPU 111) can deliver the therapeutic gas into the forward flow stream after an amount of forward flow has been measured equaling the known or determined quantity $V_{dead}$.

Following a first scenario, as another example, if $V_{exp}\geq V_{del}$ as set forth in step 716, then there are several possibilities for the portion of the reverse flow to be compensated. If $V_{dead}>V_{exp}$ as set forth in step 726, then $V_{exp}$ can be the portion of reverse flow for compensation as set forth in step 732. If $V_{exp}=V_{dead}$ as set forth in step 728, then $V_{dead}$ can be the portion of reverse flow for compensation as set forth in step 734. $V_{dead}<V_{exp}$ as set forth in step 730, then $V_{dead}$ can be the portion of reverse flow for compensation as set forth in step 736.

In at least some instance, using the above values for at least steps 732, 734, and 736, may slightly over compensate for iNO delivery, while still remaining within the specified desire dose range. This slight over delivery may occur, for example, as the initial portion of exhalation (e.g. the patient's airway dead space) may exhaust out of the patient breathing circuit via the exhaust port (e.g., exhaust port 604 illustrated in FIGS. 6A-6B), and therefore this portion of V exp may not contain iNO, for example, because lung absorption of iNO may be about 98%. Factoring in the above, the therapeutic gas device may over deliver slightly. The slight over delivery may be due to not all of the patient's airway dead space going out through the exhaust port and/or less than about 98% absorption of iNO.

Still following the above example, the NO gas monitor likely may under-report, for example, because it may be sampling portion of the gas flow that may not contain iNO. In exemplary embodiments, as described below in more detail, a carbon dioxide ($CO_2$) sensor may be used to detect the above scenario and/or compensate the iNO gas monitor readings during at least this scenario.

Following a second scenario, as yet another example, if $V_{exp}\geq V_{del}$ as set forth in step 716, then there are several possibilities for the portion of the reverse flow to be compensated. If $V_{exp}>V_{dead}$ as set forth in step 726, then no portion of reverse flow may be used and/or needed for compensation as set forth in step 732. If $V_{exp}=V_{dead}$ as set forth in step 728, then no portion of reverse flow may be used and/or needed for compensation as set forth in step 734. $V_{exp}<V_{dead}$ as set forth in step 730, then no portion of reverse flow may be used and/or needed for compensation as set forth in step 736.

In at least some instance, using the above values for at least steps 732, 734, and 736, may slightly under compensate for iNO delivery, while still remaining within the specified accuracy for the iNO delivery system. This slight under delivery may occur, for example, for at least some of the reasons stated above (e.g., first part of exhalation does not get exhausted out of the exhaust port, less absorption, etc.). Still following the above example, the NO gas monitor may under-report, for example, because it may be sampling portion of the gas flow that may not contain iNO. In exemplary embodiments, as described below in more detail, a $CO_2$, sensor may be used to detect the above scenario and/or compensate the iNO gas monitor readings during at least this scenario.

In exemplary embodiments, the therapeutic gas delivery system can automatically determine whether to follow the first or second scenario. Determination of which scenario to follow can be based on user input, ventilator selection and/or user input, and/or communication between the ventilator and the therapeutic gas delivery system, to name a few.

In exemplary embodiments, $CO_2$ sensor(s) (e.g. mainstream infrared $CO_2$ sensor) may be used to detect scenarios such as, for example, if $V_{exp}\, V_{del}$, compensate iNO delivery, and/or compensate iNO monitoring, and/or can be for various other uses. The $CO_2$, sensor can be located in close proximity of bi-directional BCG flow sensor 402 and/or sample line 131 (e.g., illustrated in FIGS. 6A-6B), or built into either the injector module and/or sample line. For example, for scenarios such as when $V_{exp}\geq V_{del}$ to compensate for iNO delivery using the $CO_2$, sensor the reverse flow volume may be detected because if $CO_2$, may be detected in the reverse flow (e.g., the later part of expiration where minimal iNO may be detected and/or where $CO_2$ may be detected as gas exchange has occurred in the lungs) then the volume of this gas containing $CO_2$ designated as $V_{CO2}$, can be used with respect to the $V_{dead}$ for example, by factoring in whether $V_{CO2}\geq V_{dead}$ and/or $V_{CO2}<V_{dead}$.

By way of example, following the above example, if $V_{CO2}\geq V_{dead}$, then no portion of reverse flow may be used and/or needed for compensation of iNO delivery. By way of another example, following the above example, if $V_{CO2}<V_{dead}$ then when flow moves forward iNO can be delivered for the reverse flow volume where $CO_2$, was detected (e.g., $V_{CO2}$ containing $CO_2$ indicative of expiratory flow where iNO was delivered during inspiration and gas exchange occurred in the lungs) then iNO delivery can be paused for the reverse flow volume where $CO_2$, was not detected (e.g., $V_{CO2}$ containing no $CO_2$, indicative of expiratory flow where iNO was delivered during inspiration but gas exchange did not occurring the lungs), and/or then iNO delivery can resume.

In exemplary embodiments, monitoring of NO can be compensated using $CO_2$ sensors. By way of yet another example, still following the above example. to compensate monitoring of NO the sampling system and/or elements of it (e.g., sample pump, NO sensor, etc.) can be deactivated and/or not activated when $CO_2$, is detected in the reverse flow and/or the sampling system and/or elements of it (e.g., sample pump, NO sensor, etc.) can be reactivated and/or activated when flow returns in the forward direction.

Furthermore, in exemplary embodiments, a $CO_2$ sensor may be used in other breathing circuit configurations that do not include a BiPAP ventilator or a single limb. For example, a $CO_2$ sensor and corresponding compensation as described above may be used in a breathing circuit having a separate inspiratory limb and expiratory limb circuit.

In exemplary embodiments, NO may not be delivered until forward flow is measured above a minimum thresh-old and/or when flow is paused for a period of time the user may be alerted. For example, the NO delivery system may not deliver NO until forward flow, as measured by the injector module, is at least above a minimum flow value (e.g. greater than 0.25 ml/min of forward flow). For another example, when the BCG flow sensor detects that flow has paused for a period of time (e.g., 0 ml/min for 10 to 30 seconds, 0 ml/min for 15 seconds, etc.) and/or negligible flow is measured for a period of time (e.g. +/−0.25 ml/min for 10 to 30 seconds, +/−0.25 ml/min for 15 seconds, etc.) the NO delivery system may not delivery NO and alert the clinician of the condition. This may be done as the above can be indicative of a ventilator placed in standby and/or an injector module connection that has undone. This feature can, at times, be used to prevent wasting of NO gas to atmosphere.

In exemplary embodiments, the iNO delivery system may revert to a ratiometrically deliver algorithm that delivers to an average injector module flow rate, such that, for example, a relatively constant flow of NO is delivered at all times through the individual high frequency pulses. In at least some instances, the iNO delivery system detects short periods of zero flow (e.g. greater than 50 milliseconds) at high frequencies (e.g. greater than 2 hertz, etc.) and/or small reverse flow volumes (e.g., less than 5 milliliters, etc.) at high frequencies (e.g., greater 2 hertz, etc.) and/or when high common mode pressure (e.g., greater than 1 PSI, etc.) is detected, which may be indicative of a high frequency ventilator being used and in response can prompt an alarm and/or the user to confirm they are using a high frequency ventilator. If confirmed and/or detected the delivery system may revert to a constant flow delivery algorithm to deliver a constant NO flow rate in proportion to the net average forward flow (e.g. taking the reverse flow and zero flow into account), for example, compensate for the high frequency ventilation.

In exemplary embodiments, using bi-directional flow sensors and/or the invention herein, the injector module may be placed in fluid communication with the breathing circuit without concern as towards which end of the injector module is the forward end or reverse end. That is, using bi-directional flow sensors and/or the invention herein can allow for easier connection of the injector module with a breathing circuit. This can be greatly important as the injector module, breathing circuit, ventilator, and/or delivery system may be assembled during times of critical care, heightened stress, and/or when time may be of the essence.

In exemplary embodiments, using the injector module without concern for directionality of the injector module relative to the flow of the breathing circuit gas, the measurement range of the bi-directional flow sensor may be equal forward and reverse (e.g. −120 to +120 SLPM).

In exemplary embodiments, systems and methods of the present invention can utilize techniques (e.g., an algorithm) that can monitor quantities of flow in each direction over a period of time to determine which direction the injector module is placed in with respect to flow of the breathing circuit gas. For example, an algorithm may be used to determine the direction the injector module may be in (with respect to the breathing circuit gas flow) as the volume of forward flow may be greater than the volume of reverse flow. After determining the orientation of the injector module with respect to breathing circuit gas flow, NO gas delivery may begin. If determined that the injector module may be oriented in reverse (e.g., with NO injection port upstream of breathing gas sensor) then the algorithm may subtract the delivered NO flow rate from the breathing gas sensor measured flow rate. This technique may be useful for many situations (e.g., enabling delivery of NO with the injector module in either orientation, etc.). For another example, if an injector module is intended to operate primarily in one orientation, systems and methods of the present invention can produce a warning to the clinician that they inserted the BCG sensor in the reverse direction.

In exemplary embodiments, systems and methods of the present invention can utilize techniques (e.g., algorithms. sensors, etc.) to ensure proper placement of the injector module in the patient breathing circuit. For example, if the patient breathing circuit includes a humidifier, systems and methods of the present invention can detect the injector modules location relative to a humidifier and/or ensure placement of injector module upstream of the humidifier. To detect and/or ensure the location of the humidifier, systems and methods of the present invention can measure humidity and/or temperature, for example, at the injector module. If humidity is too high (e.g., above about 80% relative humidity, etc.) and/or the temperature is too hot (e.g., above about 30 degrees Celsius, above about 85 degrees Fahrenheit, close to body temperature 37° C. from the heated wire circuit used to prevent condensation, etc.) then this can be indicative of incorrect placement of the injector module in the breathing circuit, such as placement in the inspiratory limb downstream of the humidifier, in the expiratory limb, and/or the "Y" piece. Exemplary temperatures indicative of improper placement include temperatures at or above any of the following: about 25, 26, 27, 28, 29, 30, 31, 32, 33, 34, 35, 36, 37, 38, 39 or 40° C. Exemplary humidities indicative of improper placement include relative humidities at or above any of the following: about 40, 45, 50, 55, 60, 65, 70, 75, 80, 85, 90, 95, 96, 97, 98, 99 or 100% relative humidity (RH). Relative humidity may be measured directly (e.g. by a humidity sensor) and/or may be measured indirectly (e.g. by a thermal conductivity sensor). In at least some embodiments, placement of the injector module at, for example, the "Y" piece can be detected when nearly equal flow in both directions is measured (e.g., indicative of inspiration and expiration). In response to an indication of incorrect placement (e.g. injector module placement downstream of humidifier, injector module placement at the Y, etc.), an alarm and/or other indication can be provided.

In exemplary embodiments, systems and methods of the present invention can utilize techniques (e.g., algorithms, sensors, etc.) to detect gases which may be significantly different in density and/or thermal conductivity than, for example, nitric oxide, oxygen, nitrogen and/or air, to name a few. For example, breathing circuit gases containing only nitrogen and/or oxygen (e.g. air, oxygen and air mixtures, pure $N_2$ gas, pure $O_2$ gas, etc.) have densities between 1.25 and 1.42 g/L at STP. Accordingly, a measured gas density below about 1.2 g/L (e.g. at or below about 1.1, 1.0 or 0.9 g/L) or above about 1.5 g/L (e.g. at or above about 1.6, 1.7 or 1.8 g/L) can be indicative of other gases being present in the breathing circuit gas. Using such techniques, systems and methods of the present invention may detect and/or prevent over delivery nitric oxide when, for example, used with anesthesia, helium mixtures, and/or with other gases and/or mixtures. By way of example, for anesthesia, if over delivery is detected, a message and/or alarm can be provided indicating to increase the amount of fresh gas flow (e.g., diluting the remaining anesthesia). By way of another example, the flow sensor can be affiliated with calibration information used to relate the sensor output to the flow of breathing circuit gas. The sensor output may, at times, vary for gases having different densities and/or thermal conductivity. When such gases are detected and/or input by a user the calibration information can be modified and/or substituted enabling flow measurement. For example, in response to detecting and/or receiving information indicative gases having different densities and/or thermal conductive (e.g., anesthesia, helium mixtures, etc.) being used and/or going to be used, the system controller can modify and/or substitute the calibration information enabling flow measurement.

In exemplary embodiments, based on at least user input and/or algorithm(s) associated with the delivery system when use with an anesthesia machine is input and/or detected, systems and methods of the present invention can ensure that a minimum average fresh gas flow is provided to the IM. By way of example. in response to user confirmation that the delivery system is being used with an anesthesia machine and/or detection of use with an anesthesia machine, the NO delivery system can prompt the user to ensure that a minimum average fresh gas flow is being flowed through the injector module and/or the anesthesia machine (e.g., in response to communication from the delivery system, in response to communication from the injector module, etc.) can provide a minimum average fresh gas flow through the injector module. The above may be done to prevent buildup of NO and/or NO2 in the circle breathing circuit affiliated with the anesthesia.

Those skilled in the art will readily recognize numerous adaptations and modifications which can be made to the therapeutic gas delivery systems and method of delivering a pharmaceutical gas of the present invention which will result in an improved method and system for introducing a known desired quantity of a pharmaceutical gas into a patient, yet all of which will fall within the scope and spirit of the present invention as defined in the following claims. Accordingly, the invention is to be limited only by the following claims and their equivalents.

Reference throughout this specification to "one embodiment," "certain embodiments," "one or more embodiments," "exemplary embodiment," "exemplary embodiments," and/ or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment," "exemplary embodiment," "exemplary embodiments," and/or "in an embodiment" in various places throughout this specification are not necessarily referring to the same embodiment of the invention. Furthermore, the particular features, structures, materials. or characteristics can be combined in any suitable manner in one or more embodiments.

It will be understood that any of the steps described can be rearranged, separated, and/or combined without deviated from the scope of the invention. For ease, steps are, at times, presented sequentially. This is merely for ease and is in no way meant to be a limitation.

Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A nitric oxide delivery system comprising:
   an injector module for delivering a therapeutic gas into a breathing gas in a breathing circuit, the injector module comprising:
      an injector body having a first opening and a second opening, the first opening and the second opening being configured to couple the injector module to the breathing circuit; and
      a therapeutic gas inlet configured to receive the therapeutic gas and enable injection of the therapeutic gas into the breathing gas in the breathing circuit flowing through the injector module;
      at least one sensor capable of measuring flow of the breathing gas in a forward direction and in a reverse direction; and
   a control module for providing the therapeutic gas to the therapeutic gas inlet, and the control module being in communication with the at least one sensor and capable of determining a volume of forward flow and reverse flow of the breathing gas based on the measurements of the at least one sensor,
   wherein the therapeutic gas flow is controlled by a control valve in communication with the therapeutic gas inlet;
   wherein the control module compensates delivery of the therapeutic gas based on the measurement from the at least one sensor such that the control module closes the control valve when the at least one sensor measures reverse flow of the breathing gas and opens the control valve after the at least one sensor measures resumed forward flow of the breathing gas and the resumed volume of forward flow is at least equal to the volume of reverse flow, and
   wherein the therapeutic gas comprises nitric oxide.

2. The nitric oxide delivery system of claim 1, wherein the at least one sensor is part of or in fluid communication with the injector module, and the control module provides an alert if the control module determines that the injector module is improperly placed in the breathing circuit.

3. The nitric oxide delivery system of claim 1, wherein the control module determines that the injector module is improperly placed in the breathing circuit if the amount of reverse flow is greater than or equal to the amount of forward flow.

4. The nitric oxide delivery system of claim 3, wherein if the amount of reverse flow is greater than the amount of forward flow, the control module determines that the injector module is placed in reverse and the control module switches the measurements for reverse flow and forward flow.

5. The nitric oxide delivery system of claim 1, wherein the system further comprises an additional sensor capable of measuring the humidity of the breathing circuit gas, and the control module determines that the injector module is improperly placed in the breathing circuit if the relative humidity of the breathing circuit gas is above 60%.

6. The nitric oxide delivery system of claim 5, wherein the additional sensor comprises humidity sensor and/or a thermal conductivity sensor.

7. The nitric oxide delivery system of claim 1, wherein the system further comprises an additional sensor capable of measuring the temperature of the breathing circuit gas, and the control module determines that the injector module is improperly placed in the breathing circuit if the temperature of the breathing circuit gas is above 25° C.

8. The nitric oxide delivery system of claim 1, wherein the system further comprises an additional sensor capable of measuring the temperature of the breathing circuit gas, and the control module determines that the injector module is improperly placed in the breathing circuit if the temperature of the breathing circuit gas is above 30° C.

9. The nitric oxide delivery system of claim 1, wherein the system further comprises an additional sensor capable of measuring a type of gas in the breathing circuit gas, and the control module compensates delivery of therapeutic gas and/or provides an alert if the control module determines that the breathing circuit gas is not air or a mixture of air and oxygen.

10. The nitric oxide delivery system of claim 9, wherein the additional sensor is capable of measuring the type of gas by measuring a density of the breathing circuit gas and/or a thermal conductivity of the breathing circuit gas.

11. The nitric oxide delivery system of claim 9, wherein the control module selects a new flow calibration curve if the control module determines that the breathing circuit gas is not air or a mixture of air and oxygen.

12. The nitric oxide delivery system of claim 9, wherein the control module prompts a user to enter a gas type if the control module determines that the breathing circuit gas is not air or a mixture of air and oxygen.

13. The nitric oxide delivery system of claim 9, wherein the control module alerts a user to raise a fresh gas flow rate at or above a patient's minute ventilation if the control module determines that the breathing circuit gas includes anesthesia gases and/or a user indicates that the breathing circuit gas includes anesthesia gases.

14. The nitric oxide delivery system of claim 1, wherein the at least one sensor is part of or in fluid communication with the injector module, and the control module receives information indicative of and/or determines a ventilator type.

15. The nitric oxide delivery system of claim 14, wherein the control module determines the ventilator type based on information regarding the breathing gas.

16. The nitric oxide delivery system of claim 15, wherein the control module determines the ventilator type is a BiPAP ventilator if the breathing circuit gas has one or more of (i) a low frequency and (ii) large volumes of reverse flow, and the control module one or more of (i) prompts a user to confirm the ventilator type, (ii) prompts a user to enter a dead space volume, (iii) prompts a user to add a carbon dioxide sensor to the breathing circuit, and (iv) prompts the user whether or not to compensate for a patient airway dead space.

17. The nitric oxide delivery system of claim 15, wherein the control module determines the ventilator type is a HFOV ventilator if the breathing circuit gas has one or more of (i) a high frequency, (ii) low volumes of reverse flow, (iii) high frequency forward flow pulses, and (iv) high common mode pressure, and the control module one or more of (i) prompts a user to confirm the ventilator type and (ii) delivers therapeutic gas ratiometrically to an average flow measured by a breathing circuit gas (BCG) flow sensor.

18. The nitric oxide delivery system of claim 15, wherein if the control module determines the ventilator type is a conventional ventilator, the control module one or more of (i) prompts a user to confirm the ventilator type and (ii) delivers therapeutic gas ratiometrically to the flow measured by a breathing circuit gas (BCG) flow sensor.

19. The nitric oxide delivery system of claim 15, wherein the control module determines the ventilator type by circuit pressure detection by using a gas injection tube in fluid communication with the therapeutic gas inlet as a pneumatic pressure sensing conduit.

20. The nitric oxide delivery system of claim 1, wherein the system further comprises a carbon dioxide sensor, and the control module compensates for monitoring of the breathing circuit gas and/or therapeutic gas delivery based on the measurement from the carbon dioxide sensor.

* * * * *